(12) United States Patent
Surh et al.

(10) Patent No.: US 11,117,958 B2
(45) Date of Patent: Sep. 14, 2021

(54) ANTI-HUMAN INTERLEUKIN-2 ANTIBODIES AND USES THEREOF

(71) Applicants: INSTITUTE FOR BASIC SCIENCE, Daejeon (KR); POSTECH ACADEMY-INDUSTRY FOUNDATION, Pohang-si (KR)

(72) Inventors: Charles D. Surh, Poway, CA (US); Jun-Young Lee, Namyangju-si (KR)

(73) Assignees: INSTITUTE FOR BASIC SCIENCE, Daejeon (KR); POSTECH ACADEMY-INDUSTRY FOUNDATION, Pohang-si (KR)

( * ) Notice: Subject to any disclaimer, the term of this patent is extended or adjusted under 35 U.S.C. 154(b) by 0 days.

(21) Appl. No.: 16/616,172

(22) PCT Filed: May 25, 2018

(86) PCT No.: PCT/KR2018/005955
§ 371 (c)(1),
(2) Date: Nov. 22, 2019

(87) PCT Pub. No.: WO2018/217058
PCT Pub. Date: Nov. 29, 2018

(65) Prior Publication Data
US 2020/0140538 A1    May 7, 2020

(30) Foreign Application Priority Data
May 25, 2017 (KR) .................. 10-2017-0064815

(51) Int. Cl.
| | |
|---|---|
| *C07K 16/24* | (2006.01) |
| *A61P 35/00* | (2006.01) |
| *A61K 39/395* | (2006.01) |
| *C07K 16/28* | (2006.01) |
| *A61K 39/00* | (2006.01) |

(52) U.S. Cl.
CPC ........ *C07K 16/246* (2013.01); *A61K 39/3955* (2013.01); *A61P 35/00* (2018.01); *C07K 16/2818* (2013.01); *A61K 2039/507* (2013.01); *C07K 2317/24* (2013.01); *C07K 2317/33* (2013.01); *C07K 2317/565* (2013.01); *C07K 2317/74* (2013.01); *C07K 2317/92* (2013.01)

(58) Field of Classification Search
CPC .................................................. C07K 16/246
See application file for complete search history.

(56) References Cited

FOREIGN PATENT DOCUMENTS

| | | |
|---|---|---|
| KR | 10-1340559 B1 | 12/2013 |
| KR | 10-2016-0122748 A | 10/2016 |
| WO | 2014/066834 A1 | 5/2014 |
| WO | 2016/005950 A1 | 1/2016 |
| WO | 2017/070561 A1 | 4/2017 |
| WO | 2017/121758 A1 | 7/2017 |

OTHER PUBLICATIONS

The extended European Search Report for the corresponding EP Application No. 18804946.4, dated Feb. 1, 2021, 7 pages.
Letourneau et al., "IL-2/anti-IL-2 antibody complexes show strong biological activity by avoiding interaction with IL-2 receptor alpha subunit CD25", PNAS, vol. 107, No. 5, pp. 2171-2176, (2010).
Rosenberg, "IL-2: The First Effective Immunotherapy for Human Cancer", The Journal of Immunology, vol. 192, pp. 5451-5458, (2014).

*Primary Examiner* — Prema M Mertz
(74) *Attorney, Agent, or Firm* — Vorys. Sater, Seymour and Pease LLP; Mih Suhn Koh

(57) ABSTRACT

Provided is an antibody that binds to human interleukin-2 (hIL-2), and more particularly to an anti-hIL-2 antibody that binds specifically to a particular epitope of hIL-2, thereby inhibiting the binding of the hIL-2 to CD25.
The anti-hIL-2 antibody of the subject matter binds specifically to a particular epitope of hIL-2, thereby inhibiting the binding of the hIL-2 to CD25, thereby minimizing expansion of Treg cells. In addition, it stimulates the $CD8^+$ T cells and NK cells that exhibit anti-tumor activity. Thus, the anti-hIL-2 antibody of the present invention is useful as a new anticancer therapeutic agent.

10 Claims, 7 Drawing Sheets
Specification includes a Sequence Listing.

SEQUENCE LISTING

<160> NUMBER OF SEQ ID NOS: 34

<210> SEQ ID NO 1

```
<211> LENGTH: 363
<212> TYPE: DNA
<213> ORGANISM: Artificial Sequence
<220> FEATURE:
<223> OTHER INFORMATION: TCB2 Heavy chain Variable region

<400> SEQUENCE: 1
gaggtgcaac tgcagcagtc tggggctgag ctggcaagac ctggggcttc agtgaagttg      60
tcctgcaagg cttctggcta cacctttact acctactgga ttcagtgggt gaaacagagg     120
cctggacagg gtctggaatg gattggggct atttatcctg agatggtga tactaggtac      180 attcagaatt tcaagggcaa ggccacattg actgcagata atcctccag cacagcctac      240 atgcaactca gcagcttggc atctgaggac tctgcggtct attactgtgc aagatccctg     300
gcaactcggg gcttctatgc tatggactac tggggtcaag aacctcagt caccgtctcc      360 tca                                                                    363

<210> SEQ ID NO 2
<211> LENGTH: 321
<212> TYPE: DNA
<213> ORGANISM: Artificial Sequence
<220> FEATURE:
<223> OTHER INFORMATION: TCB2 Light chain Variable region

<400> SEQUENCE: 2
gacattgtga tgacccagtc tccagcatcc ctgtccatgg ctataggaga aaaagtcacc      60
atcagatgca taaccagcac tgatattgat gatgatatga actggtacca gcagaagcca     120
ggggaacctc ctaagctcct tatttcagaa ggcaatactc ttcgtcctgg agtcccatcc     180
cgattctcca gcagtggcta tggtacagat tttgttttta caattgaaaa catgctctca     240
gaagatgttg cagattacta ctgtttgcaa agtgataact gccgtacac gttcggaggg      300 gggaccaagc tggaaataaa a                                                321

<210> SEQ ID NO 3
<211> LENGTH: 120
<212> TYPE: PRT
<213> ORGANISM: Artificial Sequence
<220> FEATURE:
<223> OTHER INFORMATION: TCB2 Heavy chain Variable region

<400> SEQUENCE: 3

Glu Val Gln Leu Gln Gln Ser Gly Ala Glu Leu Ala Arg Pro Gly Ala
 1               5                  10                  15

Ser Val Lys Leu Ser Cys Lys Ala Ser Gly Tyr Thr Phe Thr Thr Tyr
            20                  25                  30

Trp Ile Gln Trp Val Lys Gln Arg Pro Gly Gln Gly Glu Trp Ile Gly
        35                  40                  45

Ala Ile Tyr Pro Gly Asp Gly Asp Thr Arg Tyr Ile Gln Asn Phe Lys
    50                  55                  60

Gly Lys Ala Thr Leu Thr Ala Asp Lys Ser Ser Thr Ala Tyr Met
65                  70                  75                  80

Gln Leu Ser Ser Leu Ala Ser Glu Asp Ser Ala Val Tyr Tyr Cys Ala
                85                  90                  95

Arg Ser Leu Ala Thr Arg Gly Phe Tyr Ala Met Asp Tyr Trp Gly Gln
            100                 105                 110

Gly Thr Ser Val Thr Val Ser Ser
        115                 120
```

```
<210> SEQ ID NO 4
<211> LENGTH: 107
<212> TYPE: PRT
<213> ORGANISM: Artificial Sequence
<220> FEATURE:
<223> OTHER INFORMATION: TCB2 Light chain Variable region

<400> SEQUENCE: 4

Asp Ile Val Met Thr Gln Ser Pro Ala Ser Leu Ser Met Ala Ile Gly
1               5                   10                  15

Glu Lys Val Thr Ile Arg Cys Ile Thr Ser Thr Asp Ile Asp Asp Asp
            20                  25                  30

Met Asn Trp Tyr Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Tyr
                85                  90                  95

Thr Phe Gly Gly Gly Thr Lys Leu Glu Ile Lys
            100                 105

<210> SEQ ID NO 5
<211> LENGTH: 15
<212> TYPE: DNA
<213> ORGANISM: Artificial Sequence
<220> FEATURE:
<223> OTHER INFORMATION: TCB2 Heavy chain CDR1

<400> SEQUENCE: 5
acctactgga ttcag                                                    15

<210> SEQ ID NO 6
<211> LENGTH: 51
<212> TYPE: DNA
<213> ORGANISM: Artificial Sequence
<220> FEATURE:
<223> OTHER INFORMATION: TCB2 Heavy chain CDR2

<400> SEQUENCE: 6
gctatttatc ctggagatgg tgatactagg tacattcaga atttcaaggg c             51

<210> SEQ ID NO 7
<211> LENGTH: 36
<212> TYPE: DNA
<213> ORGANISM: Artificial Sequence
<220> FEATURE:
<223> OTHER INFORMATION: TCB2 Heavy chain CDR3

<400> SEQUENCE: 7
tccctggcaa ctcggggctt ctatgctatg gactac                             36

<210> SEQ ID NO 8
<211> LENGTH: 33
<212> TYPE: DNA
<213> ORGANISM: Artificial Sequence
<220> FEATURE:
<223> OTHER INFORMATION: TCB2 Light chain CDR1

<400> SEQUENCE: 8
ataaccagca ctgatattga tgatgatatg aac                                33
```

```
<210> SEQ ID NO 9
<211> LENGTH: 21
<212> TYPE: DNA
<213> ORGANISM: Artificial Sequence
<220> FEATURE:
<223> OTHER INFORMATION: TCB2 Light chain CDR2

<400> SEQUENCE: 9
gaaggcaata ctcttcgtcc t                                    21

<210> SEQ ID NO 10
<211> LENGTH: 27
<212> TYPE: DNA
<213> ORGANISM: Artificial Sequence
<220> FEATURE:
<223> OTHER INFORMATION: TCB2 Light chain CDR3

<400> SEQUENCE: 10
ttgcaaagtg ataacttgcc gtacacg                              27

<210> SEQ ID NO 11
<211> LENGTH: 5
<212> TYPE: PRT
<213> ORGANISM: Artificial Sequence
<220> FEATURE:
<223> OTHER INFORMATION: TCB2 Heavy chain CDR1

<400> SEQUENCE: 11

Thr Tyr Trp Ile Gln
1               5

<210> SEQ ID NO 12
<211> LENGTH: 17
<212> TYPE: PRT
<213> ORGANISM: Artificial Sequence
<220> FEATURE:
<223> OTHER INFORMATION: TCB2 Heavy chain CDR2

<400> SEQUENCE: 12

Ala Ile Tyr Pro Gly Asp Gly Asp Thr Arg Tyr Ile Gln Asn Phe Lys
1               5                   10                  15

Gly

<210> SEQ ID NO 13
<211> LENGTH: 12
<212> TYPE: PRT
<213> ORGANISM: Artificial Sequence
<220> FEATURE:
<223> OTHER INFORMATION: TCB2 Heavy chain CDR3

<400> SEQUENCE: 13

Ser Leu Ala Thr Arg Gly Phe Tyr Ala Met Asp Tyr
1               5                   10

<210> SEQ ID NO 14
<211> LENGTH: 11
<212> TYPE: PRT
<213> ORGANISM: Artificial Sequence
<220> FEATURE:
<223> OTHER INFORMATION: TCB2 Light chain CDR1

<400> SEQUENCE: 14

Ile Thr Ser Thr Asp Ile Asp Asp Asp Met Asn
1               5                   10

<210> SEQ ID NO 15
```

```
<211> LENGTH: 7
<212> TYPE: PRT
<213> ORGANISM: Artificial Sequence
<220> FEATURE:
<223> OTHER INFORMATION: TCB2 Light chain CDR2

<400> SEQUENCE: 15

Glu Gly Asn Thr Leu Arg Pro
1               5

<210> SEQ ID NO 16
<211> LENGTH: 9
<212> TYPE: PRT
<213> ORGANISM: Artificial Sequence
<220> FEATURE:
<223> OTHER INFORMATION: TCB2 Light chain CDR3

<400> SEQUENCE: 16

Leu Gln Ser Asp Asn Leu Pro Tyr Thr
1               5

<210> SEQ ID NO 17
<211> LENGTH: 5
<212> TYPE: PRT
<213> ORGANISM: Artificial Sequence
<220> FEATURE:
<223> OTHER INFORMATION: Nara1 Heavy chain CDR1

<400> SEQUENCE: 17

Asn Tyr Leu Ile Glu
1               5

<210> SEQ ID NO 18
<211> LENGTH: 17
<212> TYPE: PRT
<213> ORGANISM: Artificial Sequence
<220> FEATURE:
<223> OTHER INFORMATION: Nara1 Heavy chain CDR2

<400> SEQUENCE: 18

Val Ile Asn Pro Gly Ser Gly Gly Thr Asn Tyr Asn Glu Lys Phe Lys
1               5                   10                  15

Gly

<210> SEQ ID NO 19
<211> LENGTH: 12
<212> TYPE: PRT
<213> ORGANISM: Artificial Sequence
<220> FEATURE:
<223> OTHER INFORMATION: Nara1 Heavy chain CDR3

<400> SEQUENCE: 19

Trp Arg Gly Asp Gly Tyr Tyr Ala Tyr Phe Asp Val
1               5                   10

<210> SEQ ID NO 20
<211> LENGTH: 15
<212> TYPE: PRT
<213> ORGANISM: Artificial Sequence
<220> FEATURE:
<223> OTHER INFORMATION: Nara1 Light chain CDR1

<400> SEQUENCE: 20

Lys Ala Ser Gln Ser Val Asp Tyr Asp Gly Asp Ser Tyr Met Asn
1               5                   10                  15
```

-continued

```
<210> SEQ ID NO 21
<211> LENGTH: 7
<212> TYPE: PRT
<213> ORGANISM: Artificial Sequence
<220> FEATURE:
<223> OTHER INFORMATION: Nara1 Light chain CDR2

<400> SEQUENCE: 21

Ala Ala Ser Asn Leu Glu Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Nara1 Light chain CDR3

<400> SEQUENCE: 22

Gln Gln Ser Asn Glu Asp Pro Tyr Thr
1               5

<210> SEQ ID NO 23
<211> LENGTH: 447
<212> TYPE: PRT
<213> ORGANISM: Artificial Sequence
<220> FEATURE:
<223> OTHER INFORMATION: human chimeric TCB2 Heavy chain Variable region

<400> SEQUENCE: 23

Glu Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Thr Tyr
            20                  25                  30

Trp Ile Gln Trp Val Lys Gln Arg Pro Gly Gln Gly Leu Glu Trp Ile
        35                  40                  45

Gly Ala Ile Tyr Pro Gly Asp Gly Asp Thr Arg Tyr Ile Gln Asn Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Ser Leu Ala Thr Arg Gly Phe Tyr Ala Met Asp Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240
```

```
Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 24
<211> LENGTH: 214
<212> TYPE: PRT
<213> ORGANISM: Artificial Sequence
<220> FEATURE:
<223> OTHER INFORMATION: human chimeric TCB2 Light chain Variable region

<400> SEQUENCE: 24

Asp Ile Val Met Thr Gln Ser Pro Ala Ser Leu Ser Met Ala Ile Gly
1               5                   10                  15

Glu Lys Val Thr Ile Arg Cys Ile Thr Ser Thr Asp Ile Asp Asp Asp
            20                  25                  30

Met Asn Trp Tyr Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 321
<212> TYPE: DNA
<213> ORGANISM: Artificial Sequence
<220> FEATURE:
<223> OTHER INFORMATION: humanized TCB2_VL03463

<400> SEQUENCE: 25
gacattcaga tgacccagag cccttccagc ctgagcgcca gcgtcgggga cagagtgacc      60
attacctgca ttacctccac agacattgac gatgacatga actggtacca gcagaagcca     120
gggaaagccc ccaagctgct gatctatgag ggaaatactc tgcggcccgg cgtgcctagc     180
agattcagct cctctggctc tgggaccgat ttcacctttta caatcagttc actgcagccc     240
gaagacattg ctacatacta ttgcctgcag agcgacaacc tgccttacac cttcggggga     300
gggaccaaac tggaaatcaa a                                               321

<210> SEQ ID NO 26
<211> LENGTH: 107
<212> TYPE: PRT
<213> ORGANISM: Artificial Sequence
<220> FEATURE:
<223> OTHER INFORMATION: humanized TCB2_VL03463

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Ile Thr Ser Thr Asp Ile Asp Asp Asp
            20                  25                  30

Met Asn Trp Tyr Gln Gln Lys Pro Gly Lys Ala Pro Lys Leu Leu Ile
        35                  40                  45

Tyr Glu Gly Asn Thr Leu Arg Pro Gly Val Pro Ser Arg Phe Ser Ser
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Ser Asp Asn Leu Pro Tyr
                85                  90                  95

Thr Phe Gly Gly Gly Thr Lys Leu Glu Ile Lys
            100                 105

<210> SEQ ID NO 27
<211> LENGTH: 363
<212> TYPE: DNA
<213> ORGANISM: Artificial Sequence
<220> FEATURE:
<223> OTHER INFORMATION: humanized TCB2_VH03463

<400> SEQUENCE: 27
gaagtgcagc tggtgcagag cggagcagaa gtgaaaaagc ctggggcaag cgtgaaggtg      60
tcctgtaaag caagcggata cattcacc acatactgga tccagtgggt gaagcaggca      120
```

```
ccaggacagg gactggagtg gatgggagca atctaccctg agacggcga tacacgatat    180 attcagaact tcaaaggccg ggtgactatg accagagaca catctactag taccgtctat    240
atggagctga gctccctgag gagcgaagat accgctgtct actattgcgc ccgctctctg    300
gctacaagag ggttctacgc tatggattat tggggacagg gacactggt caccgtcagc    360 agc                                                                 363
```

```
<210> SEQ ID NO 28
<211> LENGTH: 121
<212> TYPE: PRT
<213> ORGANISM: Artificial Sequence
<220> FEATURE:
<223> OTHER INFORMATION: humanized TCB2_VH03463

<400> SEQUENCE: 28
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Ile Gln Trp Val Lys Gln Ala Pro Gly Gln Gly Leu Glu Trp Met
        35                  40                  45

Gly Ala Ile Tyr Pro Gly Asp Gly Asp Thr Arg Tyr Ile Gln Asn Phe
    50                  55                  60

Lys Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Leu Ala Thr Arg Gly Phe Tyr Ala Met Asp Tyr Trp Gly
            100                 105                 110

Gln Gly Thr Leu Val Thr Val Ser Ser
        115                 120

```
<210> SEQ ID NO 29
<211> LENGTH: 321
<212> TYPE: DNA
<213> ORGANISM: Artificial Sequence
<220> FEATURE:
<223> OTHER INFORMATION: humanized TCB2_VL2

<400> SEQUENCE: 29
```

```
gacatcgtga tgacccagag ccccagttcc ctgagcgcca gcgtcggaga cagagtgact    60
attaggtgta ttacttccac agatattgac gatgacatga actggtacca gcagaagcca    120
ggcaaagccc ccaagctgct gatcagcgag ggaaatactc tgcgaccagg agtgccttct    180
agattctctg gcagtgggta tggaaccgat ttcacctttca caatcagctc cctgcagccc    240
gaagatattg ctgactacta ttgcctgcag agcgataacc tgccatacac cttcggcggg    300
gggaccaaac tggaaatcaa a                                             321
```

```
<210> SEQ ID NO 30
<211> LENGTH: 107
<212> TYPE: PRT
<213> ORGANISM: Artificial Sequence
<220> FEATURE:
<223> OTHER INFORMATION: humanized TCB2_VL2

<400> SEQUENCE: 30
```

Asp Ile Val Met Thr Gln Ser Pro Ser Ser Leu Ser Ala Ser Val Gly
1               5                   10                  15

Asp Arg Val Thr Ile Arg Cys Ile Thr Ser Thr Asp Ile Asp Asp
            20                  25                  30

Met Asn Trp Tyr Gln Gln Lys Pro Gly Lys Ala Pro Lys Leu Leu Ile
        35                  40                  45

Ser Glu Gly Asn Thr Leu Arg Pro Gly Val Pro Ser Arg Phe Ser Gly
50                  55                  60

Ser Gly Tyr Gly Thr Asp Phe Thr Phe Thr Ile Ser Ser Leu Gln Pro
65                  70                  75                  80

Glu Asp Ile Ala Asp Tyr Tyr Cys Leu Gln Ser Asp Asn Leu Pro Tyr
                85                  90                  95

Thr Phe Gly Gly Gly Thr Lys Leu Glu Ile Lys
            100                 105

<210> SEQ ID NO 31
<211> LENGTH: 363
<212> TYPE: DNA
<213> ORGANISM: Artificial Sequence
<220> FEATURE:
<223> OTHER INFORMATION: humanized TCB2_VH1

<400> SEQUENCE: 31
caggtgcagc tggtccagtc aggagcagaa gtcaagaagc ccggagcaag cgtcaaagtg      60
tcatgcaaag caagcggata tacatttacc acatactgga tccagtgggt gcgacaggca     120
ccaggacagg gactggagtg gatgggagca atctaccctg gagacggcga tacaagatat     180
attcagaact tcaagggccg ggtgactatg accagagaca catctactag taccgtctat     240
atggagctga gctccctgag gagcgaagat accgctgtct actattgcgc ccgctctctg     300
gctacaaggg ggttctacgc aatggattac tgggggcagg ggacactggt caccgtctca     360
tca                                                                    363

<210> SEQ ID NO 32
<211> LENGTH: 121
<212> TYPE: PRT
<213> ORGANISM: Artificial Sequence
<220> FEATURE:
<223> OTHER INFORMATION: humanized TCB2_VH1

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Ile Gln Trp Val Arg Gln Ala Pro Gly Gln Gly Leu Glu Trp Met
        35                  40                  45

Gly Ala Ile Tyr Pro Gly Asp Gly Asp Thr Arg Tyr Ile Gln Asn Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Leu Ala Thr Arg Gly Phe Tyr Ala Met Asp Tyr Trp Gly
            100                 105                 110

Gln Gly Thr Leu Val Thr Val Ser Ser
        115                 120

<210> SEQ ID NO 33

```
<211> LENGTH: 363
<212> TYPE: DNA
<213> ORGANISM: Artificial Sequence
<220> FEATURE:
<223> OTHER INFORMATION: humanized TCB2_VH2

<400> SEQUENCE: 33
caggtccagc tggtccagag cggagccgag gtgaagaagc ccggagcaag cgtcaaactg      60
tcatgcaagg caagcggata cactttcacc acatactgga tccagtgggt gaagcaggca     120
ccaggacagg gactggagtg gatcggagca atctaccctg gagacggcga tacacggtat     180
attcagaact tcaaaggcag agtgactatg accgctgaca catctactag taccgtctat     240
atggagctga gctccctgag gagcgaagat accgccgtct actattgcgc ccggtctctg     300
gctacaaggg gcttttatgc tatggattat tggggacagg gcacactggt caccgtctca     360
tct                                                                   363

<210> SEQ ID NO 34
<211> LENGTH: 121
<212> TYPE: PRT
<213> ORGANISM: Artificial Sequence
<220> FEATURE:
<223> OTHER INFORMATION: humanized TCB2_VH2

<400> SEQUENCE: 34

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Thr Tyr
            20                  25                  30

Trp Ile Gln Trp Val Lys Gln Ala Pro Gly Gln Gly Leu Glu Trp Ile
        35                  40                  45

Gly Ala Ile Tyr Pro Gly Asp Gly Asp Thr Arg Tyr Ile Gln Asn Phe
    50                  55                  60

Lys Gly Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Leu Ala Thr Arg Gly Phe Tyr Ala Met Asp Tyr Trp Gly
            100                 105                 110

Gln Gly Thr Leu Val Thr Val Ser Ser
        115                 120
```

ANTI-HUMAN INTERLEUKIN-2 ANTIBODIES AND USES THEREOF

CROSS-REFERENCE TO RELATED APPLICATIONS

This application claims priority to and the benefit of Korean Patent Application No. 10-2017-0064815, filed on May 25, 2017 and International Patent Application No. PCT/KR2018/005955, filed on May 25, 2018, the disclosure of which is incorporated herein by reference in its entirety.

TECHNICAL FIELD

The present invention relates to an antibody that binds to human interleukin-2 (hIL-2), and more particularly to an anti-hIL-2 antibody that binds specifically to a particular epitope of hIL-2, thereby inhibiting the binding of the hIL-2 to CD25.

BACKGROUND ART

Interleukin-2 (IL-2) is a pleiotropic cytokine that plays an essential role in the survival, expansion and function of various lymphocytes including Treg (Foxp3$^+$ CD4$^+$ regulatory T) cells, natural killer cells (NK cells) and the like, which express IL-2 receptor. Interleukin-2 receptor (IL-2R) is present as high-affinity IL-2 receptor (IL-2R) and low-affinity IL-2 receptor (IL-2R) depending on its affinity. The high-affinity IL-2 receptor consists of three chains, IL-2Rγc (CD132), IL-2Rβ (CD122) and IL-2Rα (CD25), and the low-affinity IL-2 receptor consists only of IL-2Rγc and IL-2Rβ chains (Boyman, O., et al., Nat Rev Immunol, 2012. 12(3): p. 180-90).

Since IL-2 stimulates CD8$^+$ T cells and NK cells with anti-tumor activity, it was clinically used in the US and Europe in the 1990s for the treatment of metastatic melanoma and metastatic renal cancer (Rosenberg, S. A., J Immunol, 2014. 192(12): p. 5451-8). However, IL-2 therapy was effective in only less than 10% of cancer patients who received the therapy, and involved serious side effects. This is because IL-2 administered has a very short half-life in vivo and CD8 T cells and NK cells with anti-tumor activity express the low-affinity IL-2 receptor, and thus administration of a large amount of IL-2 is required. For this reason, serious diseases of multiple organs are caused by vascular leak syndrome and hypotension (Lotze, M. T., et al., J Immunol, 1985. 134(1): p. 157-66, Schwartz, R. N., et al., Oncology (Williston Park), 2002. 16(11 Suppl 13): p. 11-20). Another problem is that IL-2 administration induces a strong expansion of Treg cells that express the high-affinity IL-2 receptor and that inhibit anti-tumor immunity mediated by CD8$^+$ T cells and NK cells (Brandenburg, S., et al., Eur J Immunol, 2008. 38(6): p. 1643-53; Facciabene, A., et al., Cancer Res, 2012. 72(9): p. 2162-71). A method for overcoming these disadvantages of IL-2 therapy is to extend the in vivo half-life of IL-2 and, at the same time, selectively activate the CD8$^+$ T cells and NK cells that express the low-affinity IL-2 receptor. There have been many attempts to do this, but there has been little success (Arenas-Ramirez, N., et al., Sci Transl Med, 2016. 8(367): p. 367ra166).

Recently, modification of the amino acid residues of IL-2 that binds to the high-affinity IL-2 receptor has been proposed as a solution. However, this method has a limitation in that it can provide a modified IL-2 that has immunogenicity or susceptibility to proteases that degrade an artificially introduced amino acid sequence (Levin, A. M., et al., Nature, 2012. 484(7395): p. 529-33).

Accordingly, the present inventors have made extensive efforts to develop a method that extends the in vivo half-life of IL-2 without causing an unnatural modification of IL-2, and at the same time, selectively activates the CD8$^+$ T cells and NK cells that express the low-affinity IL-2 receptor. As a result, the present inventors have found that, when an anti-IL-2 monoclonal antibody (mAb) having a particular specificity is bound to IL-2, it selectively inhibits the binding of IL-2 to the high-affinity IL-2 receptor, thereby completing the present invention.

The information disclosed in the Background Art section is only for the enhancement of understanding of the background of the present invention, and therefore may not contain information that forms a prior art that would already be known to a person of ordinary skill in the art.

DISCLOSURE OF INVENTION

Technical Problem

It is an object of the present invention to provide an anti-hIL-2 antibody or antigen-binding fragment thereof, which binds specifically to human interleukin-2 (hIL-2), and inhibits the binding of the hIL-2 to CD25.

Another object of the present invention is to provide a nucleic acid encoding the anti-hIL-2 antibody or antigen-binding fragment thereof, a vector comprising the nucleic acid, a cell transformed with the vector, and a method of producing an anti-hIL-2 antibody or antigen-binding fragment thereof using the same.

Still another object of the present invention is to provide a composition and treatment method for preventing or treating cancer, which comprises the anti-hIL-2 antibody or antigen-binding fragment thereof as an active ingredient.

Yet another object of the present invention is to provide a bispecific antibody or antibody-drug conjugate comprising the anti-hIL-2 antibody or antigen-binding fragment thereof, and a composition and treatment method for preventing or treating cancer, which comprises the bispecific antibody or antibody-drug conjugate as an active ingredient.

A further object of the present invention is to provide a co-administration composition and treatment method for cancer treatment, which comprises the anti-hIL-2 antibody or antigen-binding fragment thereof and an immune checkpoint inhibitor.

Technical Solution

To achieve the above object, the present invention provides an anti-hIL-2 antibody or antigen-binding fragment thereof that comprises: a heavy-chain variable region comprising a heavy-chain CDR1 comprising an amino acid sequence of SEQ ID NO: 11, a heavy-chain CDR2 comprising an amino acid sequence of SEQ ID NO: 12, and a heavy-chain CDR3 comprising an amino acid sequence of SEQ ID NO: 13; and a light-chain variable region comprising a light-chain CDR1 comprising an amino acid sequence of SEQ ID NO: 14, a light-chain CDR2 comprising an amino acid sequence of SEQ ID NO: 15, and a light-chain CDR3 comprising an amino acid sequence of SEQ ID NO: 16.

The present invention also provides a nucleic acid encoding the anti-hIL-2 antibody or antigen-binding fragment thereof, a vector comprising the nucleic acid, a cell transformed with the vector, and a method of producing an anti-hIL-2 antibody or antigen-binding fragment thereof using the same.

The present invention also provides a complex in which the anti-hIL-2 antibody or antigen-binding fragment thereof is bound to hIL-2.

The present invention also provides a composition and treatment method for preventing or treating cancer, which comprises the anti-hIL-2 antibody or antigen-binding fragment thereof as an active ingredient.

The present invention also provides a bispecific antibody or antibody-drug conjugate comprising the anti-hIL-2 antibody or antigen-binding fragment thereof, and a composition and treatment method for preventing or treating cancer, which comprises the bispecific antibody or antibody-drug conjugate as an active ingredient.

The present invention also provides a co-administration composition and treatment method for cancer treatment, which comprises the anti-hIL-2 antibody or antigen-binding fragment thereof and an immune checkpoint inhibitor.

The present invention also provides the use of the anti-hIL-2 antibody or antigen-binding fragment thereof for the prevention or treatment of cancer.

The present invention also provides the use of the anti-hIL-2 antibody or antigen-binding fragment thereof for the preparation of a medicine for the prevention or treatment of cancer.

The present invention also provides a composition for enhancing vaccine efficacy, which comprises the anti-hIL-2 antibody or antigen-binding fragment thereof as an active ingredient.

BRIEF DESCRIPTION OF THE DRAWINGS

FIG. 2A shows the results of analyzing the frequency of immune cells; FIG. 2B shows the results of analyzing the expression of CD44 and CD62L in CD4 and CD8 T cells; FIG. 2C shows the results of experimental statistical analysis; and FIG. 2D shows the effect of a hIL-2/MAB602 or hIL-2/TCB2 complex on expansion of immune cells and the results of experimental statistical analysis ($p<0.01$, *$p<0.001$ (unpaired t test)).

BEST MODE FOR CARRYING OUT THE INVENTION

Figure 1:
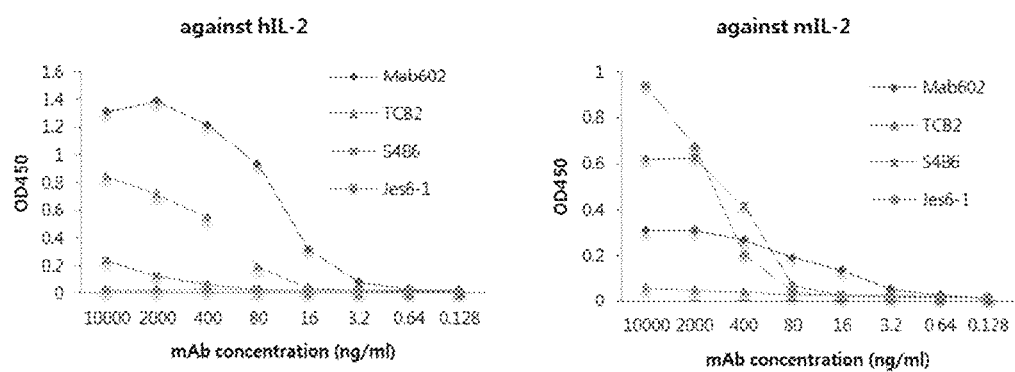
FIG. 1 shows the results of testing the binding specificity of a TCB2 monoclonal antibody against hIL-2.

Unless otherwise defined, all technical and scientific terms used herein have the same meaning as commonly understood by one of ordinary skill in the art to which the present disclosure belongs. In general, the nomenclature used herein is well known and commonly used in the art.

In the present invention, efforts have been made to develop a method that extends the in vivo half-life of IL-2 without causing an unnatural modification of IL-2, and at the same time, selectively activates the CD8$^+$ T cells and NK cells that express the low-affinity IL-2 receptor. As a result, it has been found that, when an anti-IL-2 monoclonal antibody (mAb) having a particular specificity is bound to IL-2, it selectively inhibits the binding of IL-2 to the high-affinity IL-2 receptor.

In one aspect, the present invention is directed to an anti-hIL-2 antibody (referred to as "TCB2" in the specification) or antigen-binding fragment thereof, which binds specifically to human interleukin-2 (hIL-2) and inhibits the binding of the hIL-2 to CD25.

As used herein, the term "human interleukin-2 (hIL-2)" refers to a 133-amino-acid protein (15.4 kDa) having no substantial sequence homology with any other factors.

As used herein, the term "CD25" refers to the IL-2Rα chain of IL-2 receptor. The IL-2 receptor is present as high-affinity IL-2 receptor (IL-2R) and low-affinity IL-2 receptor (IL-2R) depending on its affinity, and CD25 is a chain that is not present in the low-affinity IL-2 receptor and is present only in the high-affinity IL-2 receptor.

The term "antibody" as used in the invention refers to a substance produced by the stimulus of an antigen in immune system and its kinds are not particularly limited. Lately, the antibodies have been widely used for treating diseases. As the antibodies are very stable in vivo as well as in vitro and have a long half-life, they are favorable for mass expression and production. Also, since the antibody has intrinsically a dimer structure, it has a fairly high avidity. An intact antibody has a structure with two full-length light chains and two full-length heavy chains, and each light chain is linked to each heavy chain via a disulfide bond. The constant region of an antibody is divided into a heavy chain constant region and a light chain constant region, and the heavy chain constant region has gamma (γ), mu (μ), alpha (α), delta (δ) and epsilon (ε) types, and has gamma1 (γ1), gamma2 (γ2), gamma3 (γ3), gamma4 (γ4), alpha1 (α1) and alpha2 (α2) as its subclass. The light chain constant region has kappa (κ) and lambda (λ) types.

The antibody in the invention may include an animal-derived antibody, a chimeric antibody, a humanized antibody, or a fully human antibody. An animal-derived antibody which is produced by immunizing an animal with a desired antigen may generally trigger an immune rejection response when administered to humans for treatment purpose, and a chimeric antibody has been developed to suppress such immune rejection response. A chimeric antibody is formed by replacing the constant region of an animal-derived antibody, which is a cause of an anti-isotype response, with the constant region of a human antibody using genetic engineering methods. The chimeric antibody has considerably improved anti-isotype response in comparison with animal-derived antibodies, but animal-derived amino acids are still present in its variable regions and thus it still contains potential side effects resulting from an anti-idiotypic response. It is a humanized antibody that has been thus developed to improve such side effects. This is manufactured by grafting CDRs (complementarity determining regions) which, of the variable regions of a chimeric antibody, have an important role in antigen binding into a human antibody framework.

A "humanized antibody" as used herein includes a humanized light chain variable domain immunoglobulin and a humanized heavy chain variable domain immunoglobulin. The humanized antibody may include a constant region partially or wholly derived from (including synthetic analogs) one or more human gene sequence. A humanized antibody is expected to bind to the same target antigen as a donor antibody which supplied the CDRs. Typically, all segments or portions of the humanized antibody or immunoglobulin, with the exception of the CDRs, are substantially identical or substantially homologous to corresponding segments or portions of naturally occurring or consensus human immunoglobulin sequences. It is important in CDR grafting technology for manufacturing a humanized antibody to select an optimized human antibody which can receive best the CDR of an animal-derived antibody and for this, utilization of antibody database, analysis of crystal structure, molecule modeling technology, etc. are employed. However, although the CDR of an animal-derived antibody is grafted into an optimized human antibody framework, there are a considerable number of cases where antigen binding affinity is not preserved because there are amino acids which affect antigen binding while being positioned at the framework of the animal-derived antibody. In this regard, it may be necessary to apply an additional antibody engineering technology for restoring antigen binding affinity.

As used herein, the term "monoclonal antibody (mAb)" has the same meaning as commonly used in the technical field to the present invention pertains, and means an antibody that recognizes a single epitope on an antigen to which it binds. This contrasts with a polyclonal antibody which is a collection of different antibodies that bind to the same antigen but bind to different epitopes of the antigen. For this reason, a single antigen molecule can be bound simultaneously by multiple polyclonal antibodies, but a particular monoclonal antibody specific for the antigen can be bound by only one molecule. After being bound by the single monoclonal antibody molecule, the bound epitope is blocked, and thus can no longer be bound by other monoclonal antibodies. The monoclonal nature of antibodies is particularly suitable for use as therapeutic agents. This is because these antibodies are single, homologous molecular species, and thus can be very well characterized, can be produced reproducibly, and purified. These factors make it possible to produce products whose biological activity can be predicted with a very high level of accuracy. These factors are particularly important, because these molecules must obtain permission from authorities for therapeutic administration to mammals, particularly humans.

The term "heavy chain" as used herein may be interpreted to include a full-length heavy chain including a variable region domain VH including an amino acid sequence having a variable region sequence sufficient to confer antigen-specificity, three constant region domains CH1, CH2 and CH3, and a hinge, and a fragment thereof. Also, the term "light chain" as used herein may be interpreted to include a full-length light chain including a variable region domain VL including an amino acid sequence having a variable region sequence sufficient to confer antigen-specificity and a constant region domain CL, and a fragment thereof.

In the present invention, the anti-hIL-2 antibody or antigen-binding fragment thereof may comprise: a heavy-chain variable region comprising an amino acid sequence selected from the group consisting of SEQ ID NOS: 3, 23, 28, 32, and 34; and a light-chain variable region comprising an amino acid sequence selected from the group consisting of SEQ ID NOS: 4, 24, 26, and 30. Preferably, the anti-hIL-2 antibody or antigen-binding fragment thereof may comprise: a heavy-chain variable region of SEQ ID NO: 3 and a light-chain variable region of SEQ ID NO: 4; a heavy-chain variable region of SEQ ID NO: 23 and a light-chain variable region of SEQ ID NO: 24; a heavy-chain variable region of SEQ ID NO: 28 and a light-chain variable region of SEQ ID NO: 26; a heavy-chain variable region of SEQ ID NO: 32 and a light-chain variable region of SEQ ID NO: 30; or a heavy-chain variable region of SEQ ID NO: 34 and a light-chain variable region of SEQ ID NO: 30.

As used herein, the term "complementarity determining region (CDR)" refers to the amino acid sequence of the hypervariable region of the heavy chain or light chain of immunoglobulin. Each of the heavy and light chains may comprise three CDRs (i.e., a heavy chain CDR1, a heavy chain CDR2, and a heavy chain CDR3; and a light chain CDR1, a light chain CDR2, and a light chain CDR3). The CDR may provide important contact residues for the binding of the antibody to an antigen or an epitope.

In the present invention, the anti-hIL-2 antibody or antigen-binding fragment thereof may comprise: a heavy-chain variable region comprising a heavy-chain CDR1 comprising a DNA sequence of SEQ ID NO: 5, a heavy-chain CDR2 comprising a DNA sequence of SEQ ID NO: 6, and a heavy-chain CDR3 comprising a DNA sequence of SEQ ID NO: 7; and a light-chain variable region comprising a light-chain CDR1 comprising a DNA sequence of SEQ ID NO: 8, a light-chain CDR2 comprising a DNA sequence of SEQ ID NO: 9, and a light-chain CDR3 comprising a DNA sequence of SEQ ID NO: 10.

In the present invention, the anti-hIL-2 antibody or antigen-binding fragment thereof may comprise: a heavy-chain variable region comprising a heavy-chain CDR1 comprising an amino acid sequence of SEQ ID NO: 11, a heavy-chain CDR2 comprising an amino acid sequence of SEQ ID NO: 12, and a heavy-chain CDR3 comprising an amino acid sequence of SEQ ID NO: 13; and a light-chain variable region comprising a light-chain CDR1 comprising an amino acid sequence of SEQ ID NO: 14, a light-chain CDR2 comprising an amino acid sequence of SEQ ID NO: 15, and a light-chain CDR3 comprising an amino acid sequence of SEQ ID NO: 16.

As used herein, the term "specifically binding" has the same meaning as generally known to a person of ordinary skill in the art, indicating that an antigen and an antibody specifically interact with each other to lead to an immunological response. In the present invention, the human monoclonal antibody or its fragment has the ability to discriminate human IL-2 (hIL-2) from several other potential antigens. The discrimination is achieved such that the monoclonal antibody or its fragment binds only or to a significant extent to hIL-2 as a potential binding partner in a pool of multiple different antigens. In this regard, "bind to a significant extent to hIL-2" means that hIL-2 as a potential binding partner in a pool of a plurality of equally accessible different antigens binds with an affinity at least 10-fold, preferably 50-fold, preferably 100-fold higher than antigens other than hIL-2.

As used herein, the term "antigen-binding fragment," which is a fragment of the full structure of an immunoglobulin, refers to some of a polypeptide including a portion to which an antigen can bind. For example, it may be a scFv, a (scFv)$_2$, a Fab, a Fab' or a F(ab')$_2$, but is not limited thereto. Among the above antigen-binding fragments, a Fab, which is a structure having the light chain and heavy chain variable regions, the light chain constant region, and the heavy chain first constant region (CH1), has one antigen binding site. A Fab' differs from the Fab in that the Fab' has a hinge region including at least one cysteine residue at the C-terminal of the heavy chain $C_{H1}$ domain. A F(ab')$_2$ is produced when cysteine residues at the hinge region of Fab' are joined by a disulfide bond. A Fv is a minimal antibody fragment, having only heavy chain variable regions and light chain variable regions, and a recombinant technique for producing the Fv fragment is well known in the art. A two-chain Fv may have a structure in which heavy chain variable regions are linked to light chain variable regions by a non-covalent bond, and a single-chain Fv may generally form a dimer structure as in the two-chain Fv, wherein heavy chain variable regions are covalently bound to light chain variable regions via a peptide linker or the heavy and light chain variable regions are directly linked to each other at the C-terminals thereof. The linker may be a peptide linker including 1 to 100 or 2 to 50 any amino acids, and proper sequences thereof have been known in the art. The antigen-binding fragment may be obtained using a protease (for example, a whole antibody can be digested with papain to obtain Fab fragments, or can be digested with pepsin to obtain F(ab')$_2$ fragments), or may be prepared by a genetic recombinant technique. The antigen-binding fragment of the antibody of the present invention may be a fragment including one or more CRDs.

In the present invention, the anti-hIL-2 antibody or antigen-binding fragment thereof may induce expansion of CD8$^+$ T cells and NK cells. In an example of the present invention, it was found that the anti-hIL-2 antibody according to the present invention induced activation of CD8$^+$ T cells and NK cells and induced little expansion of Treg cells.

In another aspect, the present invention is directed to a nucleic acid encoding the anti-hIL-2 antibody or the antigen-binding fragment thereof.

In the present invention, the nucleic acid encoding the anti-hIL-2 antibody or antigen-binding fragment thereof may comprise a sequence of SEQ ID NO: 1, SEQ ID NO: 2, SEQ ID NO: 25, SEQ ID NO: 27, SEQ ID NO: 29, SEQ ID NO: 31 or SEQ ID NO: 33. Specifically, the nucleic acid encoding the heavy chain of the antibody according to the present invention may comprise a sequence of SEQ ID NO: 27, 31 or 33, and/or the nucleic acid encoding the light chain of the antibody according to the present invention may comprise a sequence of SEQ ID NO: 2, 25 or 29.

The antibody or antigen-binding fragment thereof of the present invention may be recombinantly produced by isolating the nucleic acid encoding an antibody or antigen-binding fragment thereof. The nucleic acid is isolated and inserted into a replicable vector to result in further cloning (amplification of DNA) or further expression.

As used herein, the term "Nucleic acid" has a broad meaning including DNA (gDNA and cDNA) and RNA molecules. Nucleotides, basic elements of nucleic acids, include natural nucleotides as well as analogues in which sugar or base sites are modified. The sequence of the nucleic acid encoding the heavy and light chain variable regions of the present invention may be modified. Such modifications include the addition, deletion, or non-conservative substitution or conservative substitution of nucleotides.

The nucleic acid of the present invention is interpreted to include a nucleotide sequence that exhibits substantial identity to the nucleotide sequence. The substantial identity means a nucleotide sequence showing at least 80% homology, more preferably at least 90% homology, and most preferably at least 95% homology by aligning the nucleotide sequence of the present invention with any other sequence as much as possible and analyzing the aligned sequence using algorithms commonly used in the art.

The DNA encoding the antibody can be easily separated or synthesized using conventional procedures (for example, using an oligonucleotide probe capable of specifically binding to DNA encoding the heavy chain and the light chain of the antibody).

In still another aspect, the present invention is directed to a recombinant vector including the nucleic acid.

Many vectors are available. Vector components generally include, but are not limited to, one or more of the following: a signal sequence, an origin of replication, one or more marker genes, an enhancer element, a promoter, and a transcription termination sequence.

The term "vector" as used herein, includes a plasmid vector; a cosmid vector; a bacteriophage vector; and a viral vector, e.g., an adenovirus vector, retroviral vectors, and adeno-associated viral vectors as a mean for expressing a target gene in a host cell. The nucleic acid encoding the antibody in the vector is operably linked to a promoter.

As used herein, the term "operably linked" refers to a functional linkage between a nucleic acid expression control sequence (e.g., an array of promoter, signal sequence, or transcription regulation factor binding site) and another nucleic acid sequence, and thus the control sequence controls the transcription and/or translation of the other nucleic acid sequence.

When a prokaryotic cell is used as a host, a strong promoter capable of promoting transcription (such as a tac promoter, lac promoter, lacUV5 promoter, lpp promoter, pLλ promoter, pRλ promoter, rac5 promoter, amp promoter, recA promoter, SP6 promoter, trp promoter, and T7 promoter), a ribosome binding site for initiation of translation, and a transcription/translation termination sequence are generally included. Further, for example, when a eukaryotic cell is used as a host, a promoter derived from a genome of a mammalian cell (e.g., a metallothionein promoter, a β-actin promoter, a human hemoglobin promoter and a human muscle creatine promoter) or a promoter derived from an mammalian virus (e.g., adenovirus late promoter, vaccinia virus 7.5K promoter, SV40 promoter, cytomegalovirus (CMV) promoter, HSV tk promoter, mouse mammary tumor virus (MMTV) promoter, HIV LTR promoter, epstein barr virus (EBV) promoter of moloney virus and Rous sarcoma virus (RSV) promoter) can be used, and generally have a polyadenylation sequence as a transcription termination sequence.

Optionally, the vector may be fused with another sequence in order to facilitate purification of an antibody expressed therefrom. Fused sequences include, for example, glutathione S-transferase (Pharmacia, USA), maltose binding protein (NEB, USA), FLAG (IBI, USA), and 6×His (hexahistidine; Quiagen, USA).

The vector includes an antibiotic resistance gene commonly used in the art as a selective marker, and may include, for example, genes having resistance to ampicillin, gentamicin, carbenicillin, chloramphenicol, streptomycin, kanamycin, geneticin, neomycin, and tetracycline.

In yet another aspect, the present invention is directed to a cell transformed with the recombinant vector. Cells used to produce the antibody of the present invention may be prokaryotic cells, yeasts, or other higher eukaryotic cells, but are not limited thereto.

In the present invention, as the transformed cell, the prokaryotic host cell can be used, for example, a strain belonging to the genus *Bacillus* such as *Escherichia coli*, *Bacillus subtilis*, and *Bacillus thuringiensis*, *Streptomyces*, *Pseudomonas* (for example, *Pseudomonas putida*), *Proteus mirabilis*, and *Staphylococcus* (for example, *Staphylococcus carnosus*).

Meanwhile, interest in animal cells is greatest, and an example of a useful host cell line may be, but is not limited thereto, COS-7, BHK, CHO, CHOK1, DXB-11, DG-44, CHO/-DHFR, CV1, COS-7, HEK293, BHK, TM4, VERO, HELA, MDCK, BRL 3A, W138, Hep G2, SK-Hep, MMT, TRI, MRC 5, FS4, 3T3, RIN, A549, PC12, K562, PER.C6, SP2/0, NS-0, U205, or HT1080.

In a further aspect, the present invention is directed to a method of producing an anti-hIL-2 antibody or antigen-binding fragment thereof, comprising culturing the cell, thereby expressing the anti-hIL-2 antibody or antigen-binding fragment thereof according to the present invention.

The cells can be cultured in various media.

Commercially available media can be used as a culture medium without limitation. All other essential supplements known to those skilled in the art may be included in the appropriate concentrations. Culturing conditions, e.g., temperature and pH have already been used with the selected host cells for expression, which will be apparent to those skilled in the art.

When the antibody or antigen-binding fragment thereof is recovered, impurities can be removed, e.g., by centrifugation or ultrafiltration, and the resultant can be purified, for example, by affinity chromatography. Additional purification techniques may be used, such as anion or cation exchange chromatography, hydrophobic interaction chromatography, and hydroxyl apatite chromatography.

In a still further aspect, the present invention is directed to a complex in which an anti-hIL-2 antibody or antigen-binding fragment thereof is bound to hIL-2.

In a yet further aspect, the present invention is directed to an antibody-drug conjugate (ADC) comprising a drug conjugated to the anti-hIL-2 antibody or antigen-binding fragment thereof.

An antibody-drug conjugate (ADC) requires that the anticancer drug should be stably bound to the antibody before the anticancer drug is delivered to target cancer cells. The drug delivered to the target should be released from the antibody and should induce death of the target cells. To this end, the drug should be stably bound to the antibody and, at the same time, should have enough cytotoxicity to induce death of the target cells when being released from the antibody.

In the present invention, the anti-hIL-2 antibody or antigen-binding fragment thereof and cytotoxic substances including drugs such as anticancer drugs may be linked to each other by, for example, a covalent bond, a peptide bond or the like, so that they may be used as conjugates or fusion proteins (where cytotoxic substances and/or labeling substances are proteins). The cytotoxic substance may be any substance having toxicity against cancer cells, particularly solid cancer cells, and may be one or more selected from the group consisting of, but not limited to, radioisotopes, cytotoxic compounds (small molecules), cytotoxic proteins, anticancer agents, and the like. The cytotoxic proteins may be one or more selected from the group consisting of, but not limited to, ricin, saporin, gelonin, momordin, debouganin, diphtheria toxin, and *pseudomonas* toxin. The radioisotopes may be one or more selected from the group consisting of, but not limited to, 131I, 188Rh, and 90Y. The cytotoxic compounds may be one or more selected from the group consisting of, but not limited to, duocarmycin, monomethyl auristatin E (MMAE), monomethyl auristatin F (MMAF), N2'-deacetyl-N2'-(3-mercapto-1-oxopropyl)maytansine (DM1), and PBD (Pyrrolobenzodiazepine) dimer.

In the present invention, the antibody-drug conjugate may be obtained according to a technique well known in the technical field to which the present invention pertains.

In the present invention, the antibody-drug conjugate may be one in which the antibody or antigen-binding fragment thereof is bound to the drug by a linker.

In the present invention, the linker may be a cleavable linker or a non-cleavable linker.

The linker is a region that connects between anti-hIL-2 antibody and the drug. For example, the linker is configured such that it is cleavable under intracellular conditions, that is, the drug can be released from the antibody through cleavage of the linker in an intracellular environment.

The linker can be cleaved by a cleaving agent present in an intracellular environment, for example, lysosome or endosome. The linker may be a peptide linker that can be cleaved by intracellular peptidase or protease enzyme, for example, lysosome or endosome protease. Generally, the peptide linker has a length of at least two amino acids. The cleaving agents may include cathepsin B, cathepsin D, and plasmin, and are capable of hydrolyzing the peptide to enable the drug to be released into target cells. The peptide linker can be cleaved by thiol-dependent protease cathepsin B which is highly expressed in cancer tissue. For example, the linker that is used in the present invention may be a Phe-Leu or Gly-Phe-Leu-Gly linker. In addition, the peptide linker may also be a Val-Cit or Phe-Lys linker which is cleavable by, for example, intracellular protease.

In the present invention, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used.

The linker is cleavable under reducing conditions (e.g., a disulfide linker). A variety of disulfide linkers can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene).

In the present invention, the drug and/or the drug-linker may be conjugated randomly through the lysine of the antibody or may be conjugated through a cysteine which is exposed when a disulfide bond chain is reduced. In some cases, the linker-drug may be bound through a cysteine present in a genetically engineered tag, for example, a peptide or a protein. The genetically engineered tag, for example, a peptide or a protein, may include an amino acid motif that may be recognized by, for example, isoprenoid transferase. The above-described peptide or protein has a deletion at the carboxy terminus of the peptide or protein, or has an addition at the carboxy (C) terminus of the peptide or protein through covalent bonding to a spacer unit. The peptide or the protein may be covalently bonded directly to the amino acid motif or may be linked to the amino acid motif by covalent bonding to a spacer unit. The amino acid spacer unit is composed of 1 to 20 amino acids, and is preferably a glycine unit.

The linker may include a beta-glucuronide linker which is recognized and hydrolyzed by β-glucuronidase which is present in lysosomes or is highly expressed in some tumor cells. Unlike a peptide linker, the beta-glucuronide linker has an advantage in that it has high hydrophilicity, and thus can increase the solubility of an antibody-drug conjugate when it is bound to a highly hydrophobic drug.

In addition, the linker may be a non-cleavable linker. In this case, the drug may be released through only a single step (antibody hydrolysis), thus producing, for example, an amino acid-linker-drug conjugate. This type of linker may be thioether or maleimidocaproyl, and may maintain its stability in blood.

In the present invention, the drug may be a chemotherapeutic agent, toxin, micro RNA (miRNA), siRNA, shRNA, or radioisotope. The drug that is a formulation exhibiting a pharmacological effect may be conjugated to the antibody.

The chemotherapeutic agent may be a cytotoxic agent or an immune checkpoint inhibitor. Specifically, the chemotherapeutic agent may include a chemotherapeutic agent capable of functioning as a microtubulin inhibitor, a mitotic inhibitor, a topoisomerase inhibitor, or a DNA intercalator. In addition, the chemotherapeutic agent may include an immunomodulatory compound, an anticancer agent, an antiviral agent, an antibacterial agent, an antifungal agent, an antiparasitic agent, or a combination thereof.

The drug may be one or more selected from the group consisting of, but not limited to, for example, maytansinoid, auristatin, aminopterin, actinomycin, bleomycin, talisomycin, camptothecin, N8-acetyl spermidine, 1-(2-chloroethyl)-1,2-methylsulfonyl hydrazide, esperamycin, etoposide, 6-mercaptopurine, dolastatin, tricotecene, calicheamycin, taxol, taxane, paclitaxel, docetaxel, methotrexate, vincristine, vinblastine, doxorubicin, melphalan, mitomycin A, mitomycin C, chlorambucil, duocarmycin, L-asparaginase, mercaptopurine, thioguanine, hydroxyurea, cytarabine, cyclophosphamide, ifosfamide, nitrosourea, cisplatin, carboplatin, mitomycin, dacarbazine, procarbazine, topotecan, nitrogen mustard, cytoxan, etoposide, 5-fluorouracil, bischloroethylnitrosourea (BCNU), irinotecan, camptothecin, bleomycin, idarubicin, daunorubicin, dactinomycin, plicamycin, mitoxantrone, asparaginase, vinorelbine, chlorambucil, melphalan, carmustine, lomustine, busulfan, treosulfan, decarbazine, etoposide, teniposide, topotecan, 9-aminocamptothecin, crisnatol, mitomycin C, trimetrexate, mycophenolic acid, tiazofurin, ribavirin, 5-ethynyl-1-beta-dribofuranosylimidazole-4-carboxamide (EICAR), hydroxyurea, deferoxamine, floxuridine, doxifluridine, raltitrexed, cytarabine (ara C), cytosine arabinoside, fludarabine, tamoxifen, raloxifene, megestrol, goserelin, leuprolide acetate, flutamide, bicalutamide, EB1089, CB1093, KH1060, verteporfin, phthalocyanine, photosensitizer Pe4, demethoxy-hypocrellin A, interferon-α, interferon-γ, tumor necrosis factor, gemcitabine, velcade, revamid, thalamid, lovastatin, 1-methyl-4-phenylpyridiniumion, staurosporine, actinomycin D, dactinomycin, bleomycin A2, bleomycin B2, peplomycin, epirubicin, pirarubicin, zorubicin, mitoxantrone, verapamil and thapsigargin, nuclease, and toxins derived from bacteria or animals/plants.

In the present invention, the drug may include one or more nucleophilic groups selected from the group consisting of amine, thiol, hydroxyl, hydrazide, oxime, hydrazine, thiosemicarbazone, hydrazine carboxylate and aryl hydrazide groups, which can react to form covalent bonds with the linker and the electrophilic group on a linker reagent.

In another further aspect, the present invention is directed to a bispecific antibody comprising the anti-hIL-2 antibody or antigen-binding fragment thereof.

In the present invention, the bispecific antibody means an antibody form in which one of the two arms of the antibody comprises the anti-hIL-2 antibody or antigen-binding fragment thereof according to the present invention, and the other arm comprises either an antibody specific for an antigen other than hIL-2, preferably a cancer-related antigen or an immune checkpoint protein antigen, or an antibody or antigen-binding fragment thereof which binds specifically to an immune effector cell-related antigen.

The antigen to which the antibody other than the anti-hIL-2 antibody included in the bispecific antibody binds is a cancer-related antigen or an immune checkpoint protein antigen, which may be selected from among Her2, EGFR, VEGF, VEGF-R, CD-20, MUC16, CD30, CD33, CD52, 4-1BB, TIM3, PD-1, PD-L1, CTLA4, BTLA4, EphB2, E-selectin, EpCam, CEA, PSMA, PSA, ERB3, c-MET, and the like, and the immune effector cell-related antigen may be selected from among, but not limited to, TCR/CD3, CD16 (FcγRIIIa), CD28, CD28, CD44, CD56, CD69, CD64 (FcγRI), CD89, CD11b/CD18 (CR3), and the like.

In another still further aspect, the present invention is directed to a composition for preventing or treating cancer, which comprises the anti-hIL-2 antibody or antigen-binding fragment thereof as an active ingredient.

In another yet further aspect, the present invention is directed to a composition for preventing or treating cancer, which comprises the bispecific antibody or antibody-drug conjugate as an active ingredient.

"Cancer" refers to a condition in which cells proliferate abnormally and excessively due to a problem in the function of regulating the normal division, differentiation and death of the cells, and invade the surrounding tissues and organs, thereby forming a mass and destroying or deforming the existing structures. "Solid cancer" refers to a cancer which has features distinguishable from those of blood cancer and which is composed of a mass caused by abnormal growth of cells in various solid organs, including bladder, breast, intestines, kidneys, lungs, brain, esophagus, gallbladder, ovary, pancreas, stomach, cervix, thyroid, prostate, skin and the like. "Metastatic cancer" is caused by the metastasis of cancer cells, separated from a primary cancer site, to another site through blood, lymphatic vessels or the like, and proliferation of the metastasized cancer cells. The composition of the present invention can be used for the prevention or treatment of solid cancers and/or metastatic cancers. The composition of the present invention may be used for the prevention or treatment of, but not limited to, for example, skin cancer, breast cancer, colorectal cancer, kidney cancer, lung cancer, liver cancer, brain cancer, esophageal cancer, gallbladder cancer, ovarian cancer, pancreatic cancer, stomach cancer, uterine cervical cancer, thyroid cancer, prostate cancer, and bladder cancer, but is not limited thereto.

As used herein, the term "preventing/prevention" refers to all actions that inhibit the metastasis, growth, and the like of cancers or delay the onset of cancers by administering the composition. As used herein, the term "treating/treatment" refers to any action resulting in improvements in symptoms of cancers or the beneficial alteration of cancers owing to the administration of the composition.

The composition of the present invention may further comprise a pharmaceutically acceptable carrier. The carrier that is typically used in the formulation of drugs may be one or more selected from the group consisting of, but not limited to, lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrups, methyl cellulose, methylhydroxybenzoate, propylhydroxybenzoate, talc, magnesium stearate, and mineral oil. In addition, the composition may further comprise one or more selected from the group consisting of excipients, lubricants, wetting agents, sweeteners, aromatics, emulsifiers, suspensions, and preservatives.

The composition or pharmaceutical composition of the antibody may be administered orally or parenterally. Such a parenteral administration includes intravenous injection, subcutaneous injection, intramuscular injection, intraperitoneal injection, endothelial administration, topical administration, nasal administration, intrapulmonary administration, intrarectal administration, etc. Because a protein or peptide is digested when administered orally, it is preferred that a composition for oral administration may be formulated to coat an active substance or to be protected against degradation in stomach. Also, the composition may be administered by any device which can transport active substances to target cells.

The content of the anti-hIL-2 antibody (TCB2 mAb) in the composition may vary depending on various factors such as formulation method, administration method, age, body weight, sex or pathological condition of the patient, diet, administration time, administration interval, administration route, excretion rate and reaction sensitivity. For example, a daily administration dosage of the anti-hIL-2 antibody (TCB2 mAb) may be in the range from 0.001 to 1,000 mg/kg, specifically 0.01 to 100 mg/kg, more specifically 0.1 to 50 mg/kg, but is not limited thereto. The effective dose for single administration of the anti-hIL-2 antibody (TCB2 mAb) may be formulated as one formulation in a unit-dose form or formulated in an appropriate amount, or prepared by injecting into a multiple-dose vial. The "pharmaceutically effective dose" as used herein may refer to the content or the dose of an active ingredient capable of exhibiting a desired a pharmacological effect, and can be determined variously depending on various factors such as formulation method, administration method, age, body weight, sex or pathological condition of the patient, diet, administration time, administration interval, administration route, excretion rate and reaction sensitivity.

The composition may be formulated with pharmaceutically acceptable carriers and/or excipients according to a method that can be easily carried out by a person having an ordinary skill in the art to which the present invention pertains, and may be provided in a unit-dose form or enclosed in a multiple-dose vial. Here, the formulation of the composition may be in the form of a solution, a suspension, syrup or an emulsion in oily or aqueous medium, or may be extracts, powders, granules, tablets or capsules, and may further include a dispersion agent or a stabilizer. Also, the composition may be administered individually or in combination with other therapeutic agents.

In particular, the composition including the anti-hIL-2 antibody (TCB2 mAb) includes an antibody, and thus may be formulated into immuno liposome. Liposome including an antibody may be prepared according to a method well known in the pertinent art. The immuno liposome is a lipid composition including phosphatidylcholine, cholesterol and polyethyleneglycol-derived phosphatidylethanolamine, and may be prepared by reverse phase evaporation method. For example, a Fab' fragment of the antibody may be conjugated to liposome through disulfide exchange reaction.

In another yet further aspect, the present invention is directed to a co-administration composition for cancer treatment, which comprises the anti-hIL-2 antibody or antigen-binding fragment thereof and an immune checkpoint inhibitor.

In the present invention, the immune checkpoint inhibitor (also, called "checkpoint inhibitor") may be an anti-CTLA-4 antibody or an anti-PD-1 antibody, but is not limited thereto.

As used herein, the term "co-administration" (also, called "combination") means that the anti-hIL-2 antibody or antigen-binding fragment thereof and the immune checkpoint inhibitor may be administered simultaneously, sequentially, or in reverse order, and the anti-hIL-2 antibody or antigen-binding fragment thereof and the immune checkpoint inhibitor may be administered in a combination of appropriate effective amounts of the active ingredients within the range determined by those skilled in the art.

In an example of the present invention, it was found that when the anti-CTLA-4 or anti-PD-1 antibody and the anti-hIL-2 antibody according to the present invention are treated sequentially, the growth of tumor cells is further suppressed.

The co-administration composition includes the anti-hIL-2 antibody, and the components related thereto are the same as the components included in the above-described composition for preventing or treating cancer. Thus, the description of each constitution applies equally to the co-administration composition.

In another yet further aspect, the present invention is directed to a method for prevention and/or treatment of cancer, which comprises a step of administering to a patient a therapeutically effective amount of the anti-hIL-2 antibody or antigen-binding fragment thereof, the bispecific antibody or the antibody-drug conjugate.

The composition of the present invention may be administered as an individual therapeutic agent or in combination with other therapeutic agents, and may be administered sequentially or simultaneously with conventional therapeutic agents.

Any anticancer drug, for example, cisplatin, has side effects such as cachexia, sarcopenia, muscle wasting, bone wasting or involuntary body weight loss. Thus, the present invention may include a composition or a cancer treatment method, which treats cancer while preventing, minimizing or lowering the severity, frequency or occurrence of cachexia, sarcopenia, muscle wasting, bone wasting or involuntary body weight loss.

The method comprises a step of administering a pharmaceutical composition comprising an effective amount of the anti-hIL-2 antibody of the present invention in combination with at least one anticancer agent. In particular embodiments, the present invention includes a method which treats cancer while preventing, minimizing or lowering the severity, frequency or occurrence of cachexia, sarcopenia, muscle wasting, bone wasting or involuntary body weight loss, the method comprising a step of administering to a patient a pharmaceutical composition comprising an effective amount of the anti-hIL-2 antibody of the present invention in combination with one or more anticancer agents known to induce or increase the severity, frequency or occurrence of cachexia, sarcopenia, muscle wasting, bone wasting or involuntary body weight loss.

In another yet further aspect, the present invention is directed to a method for treating cancer, which comprises a step of co-administering a composition comprising the anti-hIL-2 antibody or antigen-binding fragment thereof with an immune checkpoint inhibitor.

In the method for treating cancer according to the present invention, the anti-hIL-2 antibody or antigen-binding fragment thereof and the immune checkpoint inhibitor may be administered simultaneously, sequentially, or in reverse order. Preferably, the method may comprise the steps of: (A) treating with an immune checkpoint inhibitor; and (B) treating with the anti-hIL-2 antibody or antigen-binding fragment thereof, but is not limited thereto.

The immune checkpoint inhibitor may be an anti-CTLA-4 antibody or an anti-PD-1 antibody, but is not limited thereto. The method for treating cancer includes the composition comprising the anti-hIL-2 antibody, and the components related thereto are the same as the components included in the above-described composition. Thus, the description of each constitution applies equally to the method of treating cancer by co-administration.

In another yet further aspect, the present invention is directed to the use of the anti-hIL-2 antibody or antigen-binding fragment thereof for the prevention or treatment of cancer.

In another yet further aspect, the present invention is directed to the use of the anti-hIL-2 antibody or antigen-binding fragment thereof for the preparation of a medicine for the prevention or treatment of cancer.

In another yet further aspect, the present invention is directed to a composition for enhancing vaccine efficacy, which comprises the anti-hIL-2 antibody or antigen-binding fragment thereof as an active ingredient.

As used herein, the term "vaccine" refers to a biological agent containing an antigen that immunizes a living body, and means an immunogenic or antigenic substance that produces immunity in vivo by its administration to humans or animals in order to prevent infection.

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1: Experiment on the Binding Specificity of TCB2 Monoclonal Antibody Against hIL-2

In vivo mouse models were used to evaluate the therapeutic efficacy of a hIL-2/TCB2 mAb complex. For this reason, in order to examine whether TCB2 mAb shows cross-reactivity with mouse IL-2 (mIL-2), the binding specificity TCB2 mAb against hIL-2 was tested. First, the splenocytes of BALB/c mice immunized 3-4 times with hIL-2 over several weeks were fused with SP/2 myeloma cells. When the hybridoma colony was visualized, the culture supernatant was subjected to ELISA. 5 µg/ml of hIL-2 or mIL-2 was added to and mixed with PBS, and a total of 50 µl of the mixture was coated on an ELISA plate. Next, 200 µl of 10% FBS was added to the PBS and incubated at room temperature for 30 minutes in order to prevent non-specific binding, and a titrated dose of the monoclonal antibody was incubated for 30 minutes. The binding of the monoclonal antibody to the coated hIL-2 or mIL-2 was detected with anti-mouse IgG HRP or anti-rat IgG HRP. In each step, the plate was washed 3-5 times with 200 µl of PBS. As positive controls, commercially available monoclonal antibodies were used. As a positive control for hIL-2, Mab602 was used, and as positive controls for mIL-2, JES6-1 and S4B6 were used.

As a result, Mab602 used as the positive control for hIL-2 showed low cross-reactivity, whereas TCB2 mAb showed no cross-reactivity with mIL-2 (FIG. 1). Thus, it could be seen that TCB2 mAb did specifically bind only to hIL-2.

Example 2: In Vivo Immunostimulatory Effect of hIL-2/TCB2 Complex

MAB602, a previously reported mouse anti-hIL-2 mAb, stimulated human $CD8^+$ T cells in humanized mice, thus demonstrating the efficacy of a hIL-2/mAb complex for anticancer immunotherapy in clinical applications. However, the sequence of the CDR region of MAB602 was not published, and it is unclear whether MAB602 is an antibody which has a maximum anticancer effect when used as a hIL-2/anti-hIL-2 mAb complex. Thus, it was attempted to develop an excellent hIL-2 mAb that induces the maximum activation of $CD8^+$ T cells and NK cells and the minimum expansion of Treg cells.

Figure 2:
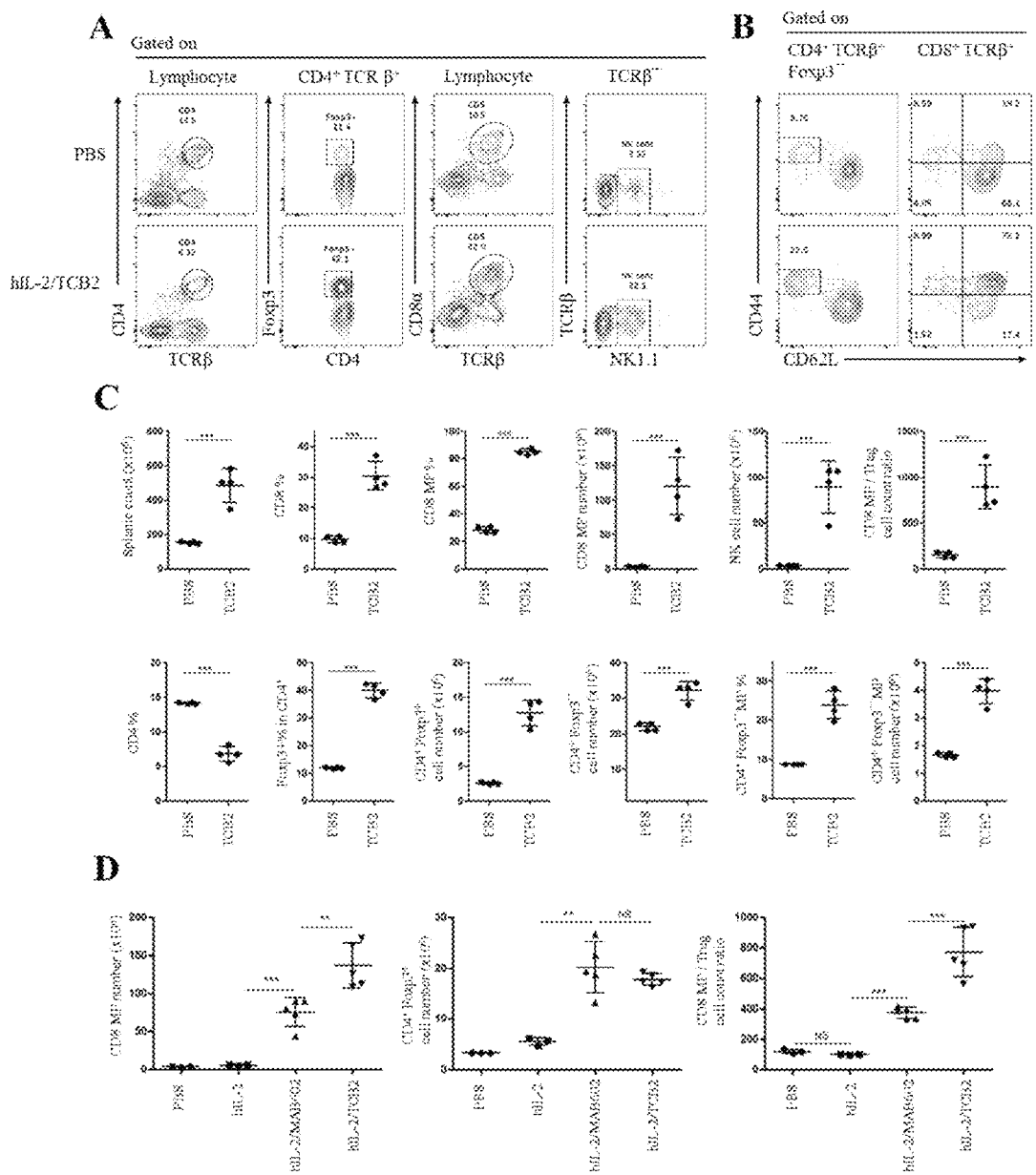
FIG. 2 shows the in vivo immunostimulatory effect of a hIL-2/TCB2 complex.

On days 0, 1, 2 and 3, a hIL-2/TCB2 mAb (0.8 µg/8 µg) complex was injected into B6 mice, and on day 5, the extent of cell expansion of splenic $CD8^+$ T cells and Treg cells was analyzed. The hIL-2/TCB2 complex minimized expansion of Treg cells and CD4 T cells, but induced a strong expansion of $CD8^+$ T cells and NK cells (FIG. 2). Specifically, when the hIL-2/TCB2 mAb complex were injected, memory phenotype (MP) $CD8^+$ T cells were about 59-fold expanded, and the expanded MP $CD8^+$ T cells constituted the majority of $CD8^+$ T cells. NK cells were also 18-fold expanded, but Treg cells were only about 5-fold expanded, which was lower than the extent of expansion of $CD8^+$ T cells and NK cells. The effective ratio of MP $CD8^+$ T cells to expanded Treg cells was 970% for the hIL-2/TCB2 mAb complex. Therefore, it can be seen that TCB2 mAb is a monoclonal antibody that selectively stimulates $CD8^+$ T cells and NK cells, not Treg cells.

In addition, the effective ratio of MP $CD8^+$ T cells to expanded Treg cells was 970% for the hIL-2/TCB2 mAb complex, but 530% for the hIL-2/MAB602 complex (FIG. 2D). Thus, TCB2 is a monoclonal antibody superior to MAB602.

Example 3: Analysis of the Affinity of TCB2 for hIL-2

The selective stimulation of $CD8^+$ T cells and NK cells by the TCB2 antibody requires that the antibody be bound to the epitope of hIL-2. Since the epitope of hIL-2 is also recognized by high-affinity IL-2R (CD25), TCB2 is likely to bind to hIL-2 near a site to which the IL-2Rα chain binds. Since MAB602 is also likely to bind to hIL-2 near a site to which the IL-2Rα chain binds, TCB2 was analyzed competitively with MAB602 in order to observe the specificity of TCB2 which is an anti-hIL-2 mAb. Another anti-hIL-2 mAb (5344.111), which is available commercially and known to bind to an epitope different from an epitope to which MAB602 binds, was used as a control.

For detection of hIL-2, sandwich ELISA was used. 900 RU (Rmax=90) of anti-hIL-2 clones were immobilized on a CM5 chip by amine coupling. A 2-fold dilution (100 nM) of hIL-2 was allowed to flow on the chip at a rate of 10 µl/min for 3 minutes, and then dissociation of the hIL-2 was monitored for 10 minutes.

Figure 3:
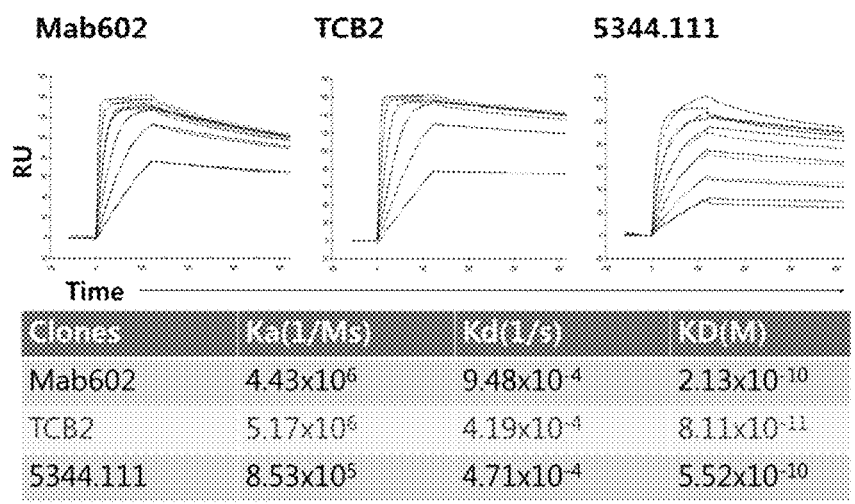
FIG. 3 shows surface plasmon resonance curves obtained using Biacore T100 for the affinities of anti-hIL-2 mAbs for hIL-2.

From the competitive analysis, it was found that TCB2 competed with MAB602. It was shown that, due to its specificity, TCB2 mAb did not compete with 5344.111, but completed with MAB602. As a result, it was confirmed that TCB2 had a higher affinity for human IL-2 than other anti-hIL-2 mAbs (FIG. 3).

Example 4: Anti-Tumor Effect of hIL-2/TCB2 Complex

Example 4-1: Effect of TCB2 mAb Against Solid Tumor

In order to demonstrate the clinical usefulness of TCB2 mAb against a solid tumor, $1\times10^6$ B16F10 melanoma cells were injected subcutaneously into B6 mice, and then PBS, hIL-2 (0.8 µg) alone or the hIL-2/TCB2 (0.8 µg/8 µg) complex was injected on days 4 to 7. Next, tumor progression was monitored for 7 days.

Figure 4:
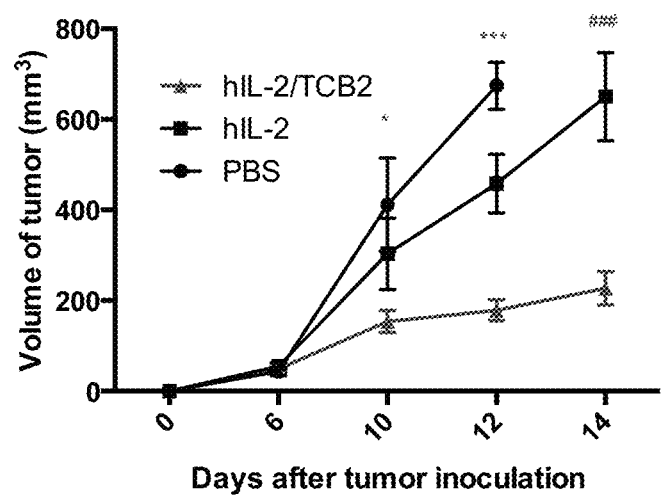
FIG. 4 shows the effect of a hIL-2/TCB2 complex against a solid tumor (***$p<0.001$ (Two way ANOVA for day 12, unpaired t test for day 14)).

As a result, inhibition of solid tumor growth had a correlation with the magnitude of cytokine-induced expansion of $CD8^+$ T cells and NK cells (FIG. 4). The hIL-2/TCB2 mAb complex inhibited tumor growth better than hIL-2 alone.

Example 4-2: Effect of TCB2 mAb Against Metastatic Tumor

In order to demonstrate the clinical usefulness of TCB2 mAb against a metastatic tumor, $3\times10^3$ B16F10 melanoma cells were injected intravenously into B6 mice. 7 Days after tumor injection, hIL-2 alone (0.8 µg) or the hIL-2/TCB2 (0.8µ/8 µg) complex was injected from day 7 to day 10. On day 18, the number of pulmonary tumor nodules was measured.

Figure 5:
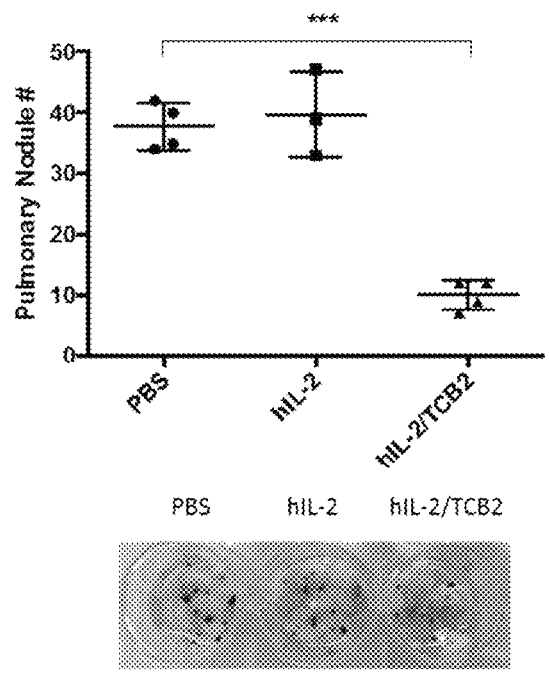
FIG. 5 shows the effect of TCB2 mAb against a metastatic tumor (***$p<0.001$ (unpaired t test)).

As a result, inhibition of the hIL-2/TCB2 well inhibited of pulmonary tumor nodules, unlike hIL-2 (FIG. 5). Thus, it can be see that TCB2 mAb has a potent anticancer effect when used as the hIL-2/TCB2 mAb complex.

Example 5: Analysis of the Effect of Combination of hIL-2/TCB2 Complex and Other Anticancer Therapies Anticancer therapies, which are currently developed worldwide, include a method that immunizes patients with a tumor neo-antigen, and a method that uses checkpoint inhibitors such as anti-CTLA-4 antibodies or anti-PD-1 antibodies. In this Example, whether the hIL-2/TCB2 complex can be used in combination with these anticancer therapies was analyzed.

Example 5-1: Effect of Combination of hIL-2/TCB2 Complex and Anticancer Therapy Based on Neo-Antigen In order to test the compatibility of the hIL-2/TCB2 complex with neo-antigen-based therapy, $1\times10^6$ B16F10 cells were injected subcutaneously into B6 mice on day 0. Next, PBS or a mixture of TRP2 peptide (100 µg) and Poly I:C (100 µg) was injected on days 3 and 7. The hIL-2/TCB2 complex (0.8 µg/8 µg) was injected in two rounds of four daily injections on days 4 to 7 and days 11 to 14. Next, tumor progression was monitored for 5 days.

Figure 6:
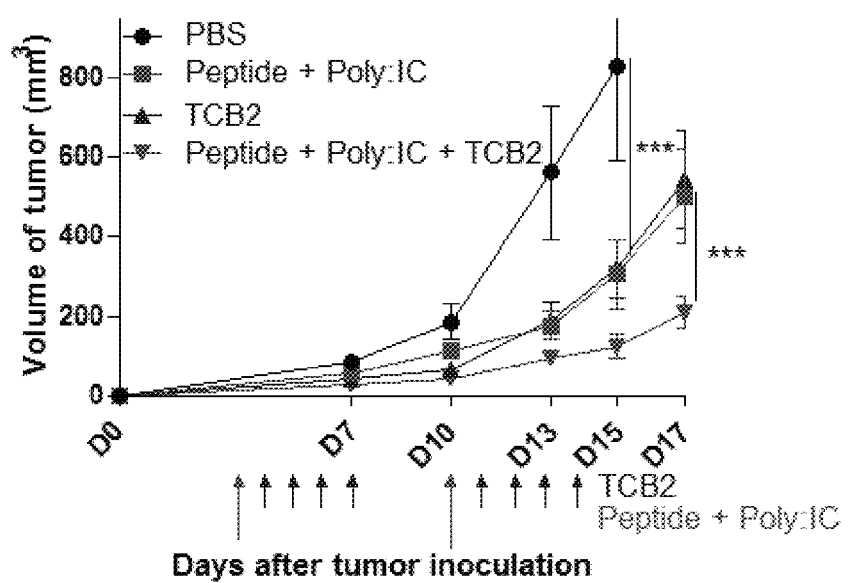
FIG. 6 shows the anti-tumor effect of a combination of a hIL-2/TCB2 complex and tumor peptide therapy in B6F10 melanoma models (***$p<0.001$ (Two way ANOVA)).

As a result, injection of the hIL-2/TCB2 complex and the neo-antigen-based therapy inhibited the growth of the B16F10 tumor to similar extents. However, when the mice were co-treated with the hIL-2/TCB2 complex and the neo-antigen-based therapy, tumor growth was more inhibited (FIG. 6). Thus, it can be seen that the hIL-2/TCB2 complex can be used in combination with the neo-antigen-based therapy.

Example 5-2: Effect of Combination of hIL-2/TCB2 Complex and Checkpoint Inhibitor To test whether the hIL-2/TCB2 complex can be used in combination with checkpoint inhibitors, CT26 (Balb/C colon cancer and MC38 (B6 colon cancer) models were used. After treatment with the hIL-2/TCB2 complex in combination with anti-CTLA-4 antibody or anti-PD-1 antibody or treatment with each of these antibodies, tumor growth was observed.

Figure 7:
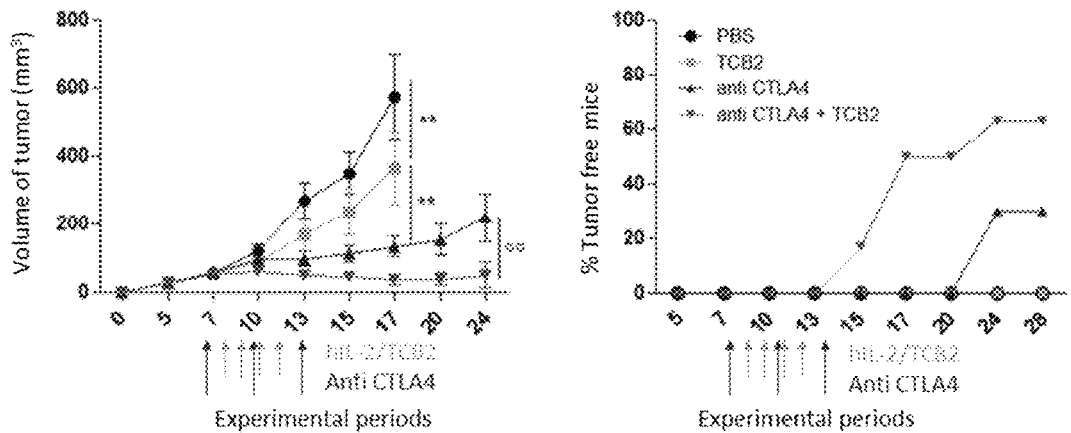
FIG. 7 shows the anti-tumor effect of a combination of a hIL-2/TCB2 complex and an anti-CTLA-4 antibody in CT26 tumor models (Balb/C colon cancer) (**$p<0.01$ (Two way ANOVA for day 17, unpaired t test for day 24)).

For an experiment in which mice were treated with the hIL-2/TCB2 complex in combination with the anti-CTLA-4 antibody, $5\times10^3$ CT26 cells were injected subcutaneously into Balb/C mice (day 0), and the anti-CTLA-4 antibody (100 µg) was injected three times at 3-day intervals from day 7. The hIL-2/TCB2 complex (0.8 µg/8 µg) was injected once a day from day 8 to day 11 (four times). As a result, the anti-CTLA-4 antibody strongly inhibited growth of the CT26 tumor, and the tumor was rejected in 33% of the mice. In the mice injected with the hIL-2/TCB2 complex, tumor growth was less inhibited than that in the mice injected with the anti-CTLA-4 antibody. However, when the mice were treated with the anti-CTLA-4 antibody combination with the hIL-2/TCB2 complex, tumor growth was more inhibited than treatment with the anti-CTLA-4 antibody, and the tumor was rejected in 63% of the mice (FIG. 7).

Figure 8:
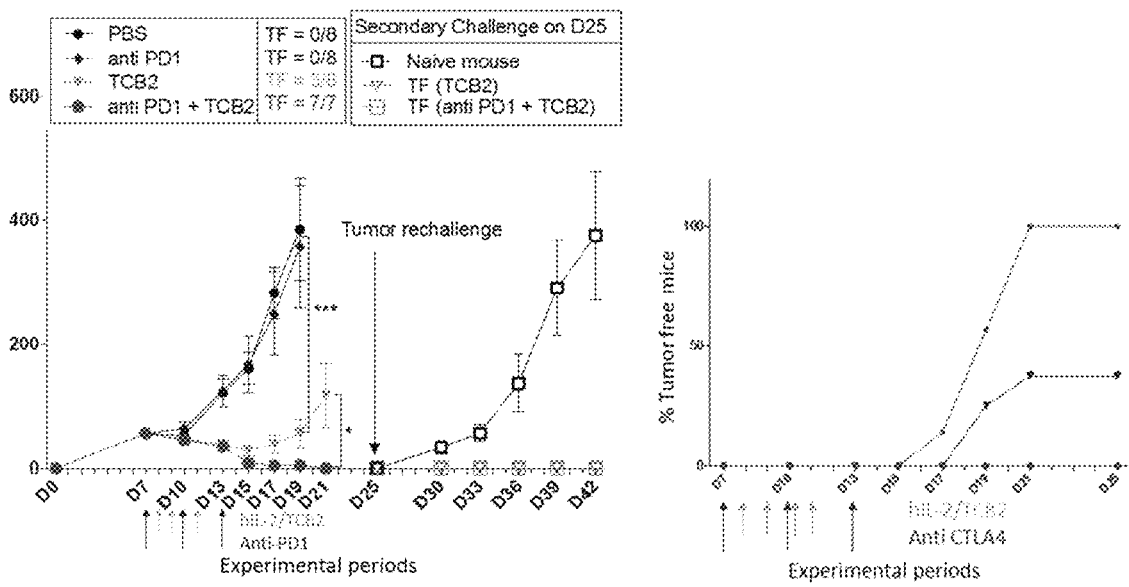
FIG. 8 shows the anti-tumor effect of a combination of a hIL-2/TCB2 complex and an anti-PD-1 antibody in MC38 tumor models (B6 colon cancer) (*$p<0.05$, **$p<0.01$ (Two way ANOVA for day 19, unpaired t test for day 21)).

For an experiment in which mice were treated with the hIL-2/TCB2 complex in combination with the anti-PD-1 antibody, $5\times10^3$ MC38 cells were injected subcutaneously into B6 mice (day 0). Then, the anti-PD-1 antibody (100 µg) was injected three times at 3-day intervals from day 7, and the hIL-2/TCB2 complex (1.5 µg/15 µg) was injected once a day from day 8 to day 11 (four times). As a result, treatment with the anti-PD-1 antibody was not effective in delaying tumor growth (the anti-PD-1 antibody was used at a dose lower than the optimum dose), but treatment with the hIL-2/TCB2 complex strongly inhibited the growth of the MC38 tumor and rejected the tumor in 37% of the mice. When the hIL-2/TCB2 complex and the anti-PD-1 antibody were injected together, the tumor was rejected in 100% of the mice (FIG. 8).

Example 5-3: Effect on Memory Response Acquisition in Immune Anticancer Therapy with hIL-2/TCB2 Complex In order to examine whether mice that rejected a tumor would acquire a memory response to the same tumor, $5\times10^3$ MC38 cells were injected into naïve B6 mice (that have never been inoculated with a tumor) or the mice that rejected the tumor by hIL-2/TCB2 in Example 5-2 (day 25). The MC38 tumor grew rapidly in the naïve B6 mice injected with it, but it did not grow in the mice that rejected the tumor (FIG. 8). This suggests that immunotherapy with the hIL-2/TCB2 complex is particularly helpful in preventing cancer recurrence in patients.

Taking these results together, it can be seen that the hIL-2/TCB2 complex may be used in combination with checkpoint inhibitors such as anti-CTLA-4 antibody or anti-PD-1 antibody and is more effective when used in combination with these checkpoint inhibitors.

Example 6: Sequencing of TCB2 Monoclonal Antibody

The complementarity determining region (CDR) of TCB2 mAb was sequenced (Tables 1 to 3).

It can be seen that the amino acid sequence of TCB2 differs from that of Nara1 (Table 4) which is an anti-hIL-mAb antibody recently developed by Onur Boyman and Natalia Ramirez (WO 2016005950 A1). The CDR similarities between TCB2 and Nara1 are 40%, 52.94% and 8.33% for heavy-chain CDRs 1 to 3, respectively, and 33.33%, 14.28% and 55.55% for light-chain CDRs 1 to 3 (Table 5).

TABLE 1

DNA sequence and amino Acid Sequence of variable region of TCB2 antibody

| | Heavy chain | Light chain |
|---|---|---|
| DNA sequence of variable region of TCB2 | GAGGTGCAACTGCAGCAGTCTGGGG CTGAGCTGGCAAGACCTGGGGCTTC AGTGAAGTTGTCCTGCAAGGCTTCT GGCTACACCTTTACTACCTACTGGA TTCAGTGGGTGAAACAGAGGCCTGG ACAGGGTCTGGAATGGATTGGGCT ATTTATCCTGGAGATGGTGATACTA GGTACATTCAGAATTTCAAGGGCAA GGCCACATTGACTGCAGATAAATCC TCCAGCACAGCCTACATGCAACTCA GCAGCTTGGCATCTGAGGACTCTGC GGTCTATTACTGTGCAAGATCCCTG GCAACTCGGGGCTTCTATGCTATGG ACTACTGGGGTCAAGGAACCTCAGT CACCGTCTCCTCA (SEQ ID NO: 1) | GACATTGTGATGACCCAGTCTCC AGCATCCCTGTCCATGGCTATAG GAGAAAAAGTCACCATCAGATGC ATAACCAGCACTGATATTGATGA TGATATGAACTGGTACCAGCAGA AGCCAGGGGAACCTCCTAAGCTC CTTATTTCAGAAGGCAATACTCT TCGTCCTGGAGTCCCATCCCGAT TCTCCAGCAGTGGCTATGGTACA GATTTTGTTTTTACAATTGAAAA CATGCTCTCAGAAGATGTTGCAG ATTACTACTGTTTGCAAAGTGAT AACTTGCCGTACACGTTCGGAGG GGGGACCAAGCTGGAAATAAAA (SEQ ID NO: 2) |
| Amino Acid Sequence of variable region of TCB2 | EVQLQQSGAELARPGASVKLSCKAS GYTFTTYWIQWVKQRPGQGEWIGAI YPGDGDTRYIQNFKGKATLTADKSS STAYMQLSSLASEDSAVYYCARSLA TRGFYAMDYWGQGTSVTVSS (SEQ ID NO: 3) | DIVMTQSPASLSMAIGEKVTIRC ITSTDIDDDMNWYQQKPGEPPKL LISEGNTLRPGVPSRFSSSGYGT DFVFTIENMLSEDVADYYCLQSD NLPYTFGGGTKLEIK (SEQ ID NO: 4) |

TABLE 2

CDR DNA sequence of TCB2 antibody

| Variable region | CDR | DNA sequence | SEQ ID NO: |
|---|---|---|---|
| Heavy chain | CDR1 | ACCTACTGGATTCAG | 5 |
| | CDR2 | GCTATTTATCCTGGAGATGGTGATACTAGGTACATTCAGAATTTCAAGGGC | 6 |
| | CDR3 | TCCCTGGCAACTCGGGGCTTCTATGCTATGGACTAC | 7 |
| Light chain | CDR1 | ATAACCAGCACTGATATTGATGATGATATGAAC | 8 |
| | CDR2 | GAAGGCAATACTCTTCGTCCT | 9 |
| | CDR3 | TTGCAAAGTGATAACTTGCCGTACACG | 10 |

TABLE 3

CDR amino acid sequence of TCB2 antibody

| Variable region | CDR | Amino acid sequence | SEQ ID NO: |
|---|---|---|---|
| Heavy chain | CDR1 | TYWIQ | 11 |
| | CDR2 | AIYPGDGDTRYIQNFKG | 12 |
| | CDR3 | SLATRGFYAMDY | 13 |
| Light chain | CDR1 | ITSTDIDDDMN | 14 |
| | CDR2 | EGNTLRP | 15 |
| | CDR3 | LQSDNLPYT | 16 |

TABLE 4

CDR amino acid sequence of Nara1 antibody

| Variable region | CDR | Amino acid sequence | SEQ ID NO: |
|---|---|---|---|
| Heavy chain | CDR1 | NYLIE | 17 |
| | CDR2 | VINPGSGGTNYNEKFKG | 18 |
| | CDR3 | WRGDGYYAYFDV | 19 |
| Light chain | CDR1 | KASQSVDYDGDSYMN | 20 |
| | CDR2 | AASNLES | 21 |
| | CDR3 | QQSNEDPYT | 22 |

TABLE 5

Comparison of CDR amino acid sequence between TCB2 and Nara1 antibodies

| Variable region | CDR | Number of the same residues of Nara1 and TCB2 | Length of amino acid of Nara1 | Similarity (%) |
|---|---|---|---|---|
| TCB2 Heavy chain | CDR1 | 2 | 5 | 40 |
| | CDR2 | 9 | 17 | 52.94 |
| | CDR3 | 1 | 12 | 8.33 |
| TCB2 Light chain | CDR1 | 5 | 15 | 33.33 |
| | CDR2 | 1 | 7 | 14.28 |
| | CDR3 | 5 | 9 | 55.55 |

Based on the sequencing data, the Fab region of TCB2 mAb was cloned into an IgG2 expression vector. The amino acid sequence of the cloned vector is shown in Table 6 below.

TABLE 6

Amino acid sequence of human chimeric TCB2

| | Amino acid sequence |
|---|---|
| Heavy chain | EVQLQQSGAELARPGASVKLSCKASGYTFTTYWIQWVKQRPGQ GLEWIGAIYPGDGDTRYIQNFKGKATLTADKSSSTAYMQLSSL ASEDSAVYYCARSLATRGFYAMDYWGQGTSVTVSSASTKGPSV FPLAPCSRSTSESTAALGCLVKDYFPEPVTVSWNSGALTSGVH TFPAVLQSSGLYSLSSVVTVPSSNFGTQTYTCNVDHKPSNTKV DKTVERKCCVECPPCPAPPVAGPSVFLFPPKPKDTLMISRTPE VTCVVVDVSHEDPEVQFNWYVDGVEVHNAKTKPREEQFNSTFR VVSVLIVVHQDWLNGKEYKCKVSNKGLPAPIEKTISKTKGQPR EPQVYTLPPSREEMTKNQVSLTCLVKGFYPSDIAVEWESNGQP ENNYKTTPPMLDSDGSFFLYSKLTVDKSRWQQGNVFSCSVMHE ALHNHYTQKSLSLSPGK (SEQ ID NO: 23) |

TABLE 6-continued

Amino acid sequence of human chimeric TCB2

| | Amino acid sequence |
|---|---|
| Light chain | DIVMTQSPASLSMAIGEKVTIRCITSTDIDDDMNWYQQKPGEP PKLLISEGNTLRPGVPSRFSSSGYGTDFVFTIENMLSEDVADY YCLQSDNLPYTFGGGTKLEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC (SEQ ID NO: 24) |

Example 7: Humanized TCB2 Antibody

In order to reduce the host immune response to mouse IgG, TCB2 mAb was humanized and expressed with human IgG1 Fc (Table 7). The CDR of mouse TCB2 (mTCB2) was introduced into the variable region of human IgG. Then, for an in vivo experiment, three humanized TCB2 (hnTCB2) mAb clones (VH1+VL2, VH2+VL2, and AH03463 (VL03463+VH03463)) having the highest affinity were selected (Table 8).

TABLE 7

DNA sequence and amino acid sequence of variable region of humanized TCB2

| | | DNA sequence | Amino acid sequence |
|---|---|---|---|
| VL03463 | Light Chain | GACATTCAGATGACCCAGAGCCCTTCCAGCC TGAGCGCCAGCGTCGGGGACAGAGTGACCAT TACCTGCATTACCTCCACAGACATTGACGAT GACATGAACTGGTACCAGCAGAAGCCAGGGA AAGCCCCCAAGCTGCTGATCTATGAGGGAAA TACTCTGCGGCCCGGCGTGCCTAGCAGATTC AGCTCCTCTGGCTCTGGGACCGATTTCACCT TTACAATCAGTTCACTGCAGCCCGAAGACAT TGCTACATACTATTGCCTGCAGAGCGACAAC CTGCCTTACACCTTCGGGGGAGGGACCAAAC TGGAAATCAAA (SEQ ID NO: 25) | DIQMTQSPSSLSA SVGDRVTI$\underline{\text{T}}$CITS TDIDDDMNWYQQK PGKAPKLLI$\underline{\text{Y}}$EGN TLRPGVPSRF$\underline{\text{SS}}$S G$\underline{\text{S}}$GTDFTFTISSL QPEDIA$\underline{\text{T}}$YYCLQS DNLPYTFGGGTKL EIK (SEQ ID NO: 26) |
| VH03463 | Heavy Chain | GAAGTGCAGCTGGTGCAGAGCGGAGCAGAAG TGAAAAAGCCTGGGGCAAGCGTGAAGGTGTC CTGTAAAGCAAGCGGATATACATTCACCACA TACTGGATCCAGTGGGTGAAGCAGGCACCAG GACAGGGACTGGAGTGGATGGGAGCAATCTA CCCTGGAGACGGCGATACACGATATATTCAG AACTTCAAAGGCCGGGTGACTATGACCAGAG ACACATCTACTAGTACCGTCTATATGGAGCT GAGCTCCCTGAGGAGCGAAGATACCGCTGTC TACTATTGCGCCCGCTCTCTGGCTACAAGAG GGTTCTACGCTATGGATTATTGGGGACAGGG GACACTGGTCACCGTCAGCAGC (SEQ ID NO: 27) | $\underline{\text{E}}$VQLVQSGAEVKK PGASVK$\underline{\text{VS}}$CKASG YTFTTYWIQWV$\underline{\text{KQ}}$ APGQGLEWMGAIY PGDGDTRYIQNFK GRVTMTRDTSTST VYMELSSLRSEDT AVYYCARSLATRG FYAMDYWGQGTLV TVSS (SEQ ID NO: 28) |
| VL2 | Light Chain | GACATCGTGATGACCCAGAGCCCCAGTTCCC TGAGCGCCAGCGTCGGAGACAGAGTGACTAT TAGGTGTATTACTTCCACAGATATTGACGAT GACATGAACTGGTACCAGCAGAAGCCAGGCA AAGCCCCCAAGCTGCTGATCAGCGAGGGAAA TACTCTGCGACCAGGAGTGCCTTCTAGATTC TCTGGCAGTGGGTATGGAACCGATTTCACCT TTACAATCAGCTCCCTGCAGCCCGAAGATAT TGCTGACTACTATTGCCTGCAGAGCGATAAC CTGCCATACACCTTCGGCGGGGGGACCAAAC TGGAAATCAAA (SEQ ID NO: 29) | DIVMTQSPSSLSA SVGDRVTIRCITS TDIDDDMNWYQQK PGKAPKLLISEGN TLRPGVPSRFSGS GYGTDFTFTISSL QPEDIADYYCLQS DNLPYTFGGGTKL EIK (SEQ ID NO: 30) |
| VH1 | Heavy Chain | CAGGTGCAGCTGGTCCAGTCAGGAGCAGAAG TCAAGAAGCCCGGAGCAAGCGTCAAAGTGTC ATGCAAAGCAAGCGGATATACATTTACCACA TACTGGATCCAGTGGGTGCGACAGGCACCAG GACAGGGACTGGAGTGGATGGGAGCAATCTA CCCTGGAGACGGCGATACAAGATATATTCAG AACTTCAAGGGCCGGGTGACTATGACCAGAG ACACATCTACTAGTACCGTCTATATGGAGCT | QVQLVQSGAEVKK PGASVKVSCKASG YTFTTYWIQWVRQ APGQGLEWMGAIY PGDGDTRYIQNFK GRVTMTRDTSTST VYMELSSLRSEDT AVYYCARSLATRG |

TABLE 7-continued

DNA sequence and amino acid sequence of
variable region of humanized TCB2

| | | DNA sequence | Amino acid sequence |
|---|---|---|---|
| | | GAGCTCCCTGAGGAGCGAAGATACCGCTGTC<br>TACTATTGCGCCCGCTCTCTGGCTACAAGGG<br>GGTTCTACGCAATGGATTACTGGGGGCAGGG<br>GACACTGGTCACCGTCTCATCA<br>(SEQ ID NO: 31) | FYAMDYWGQGTLV<br>TVSS<br>(SEQ ID NO: 32) |
| VH2 | Heavy<br>Chain | CAGGTCCAGCTGGTCCAGAGCGGAGCCGAGG<br>TGAAGAAGCCCGGAGCAAGCGTCAAACTGTC<br>ATGCAAGGCAAGCGGATACACTTTCACCACA<br>TACTGGATCCAGTGGGTGAAGCAGGCACCAG<br>GACAGGGACTGGAGTGGATCGGAGCAATCTA<br>CCCTGGAGACGGCGATACACGGTATATTCAG<br>AACTTCAAAGGCAGAGTGACTATGACCGCTG<br>ACACATCTACTAGTACCGTCTATATGGAGCT<br>GAGCTCCCTGAGGAGCGAAGATACCGCCGTC<br>TACTATTGCGCCCGGTCTCTGGCTACAAGGG<br>GCTTTTATGCTATGGATTATTGGGGACAGGG<br>CACACTGGTCACCGTCTCATCT<br>(SEQ ID NO: 33) | QVQLVQSGAEVKK<br>PGASVK<u>L</u>SCKASG<br>YTFTTYWI<u>Q</u>WV<u>KQ</u><br>APGQGLEW<u>I</u>GAIY<br>PGDGDTRYIQNFK<br>GRVTMT<u>A</u>DTSTST<br>VYMELSSLRSEDT<br>AVYYCARSLATRG<br>FYAMDYWGQGTLV<br>TVSS<br>(SEQ ID NO: 34) |

Residues in the amino acid sequence of VL03463, which were different from those in VL2, were underlined. For comparison of the sequence of the heavy-chain region, residues in VH2 and VH03463, which were different from those in VH1, were underlined. VL2 was used together with VH1 or VH2 to express two different humanized TCB2 antibodies (VL2+VH1 or VL2+VH2).

TABLE 8

Affinity of humanized TCB2 for hIL-2

| | mAbs | Ka (1/Ms) | Kd (1/s) | KD (M) | Relative similarity of humanized TCB2 to chimeric TCB2 |
|---|---|---|---|---|---|
| Set 1 | Chimeric | 2.27E+07 | 1.63E−03 | 7.17E−11 | |
| | VH1 + VL2 | 1.89E+07 | 1.97E−03 | 1.04E−10 | 68.9% |
| | VH2 + VL2 | 1.68E+07 | 4.63E−03 | 2.75E−10 | 26% |
| Set 2 | Chimeric | 2.29E+07 | 1.41E−03 | 6.16E−11 | |
| | AH03463 | 2.11E+07 | 4.18E−03 | 1.98E−10 | 31% |

Figure 9:
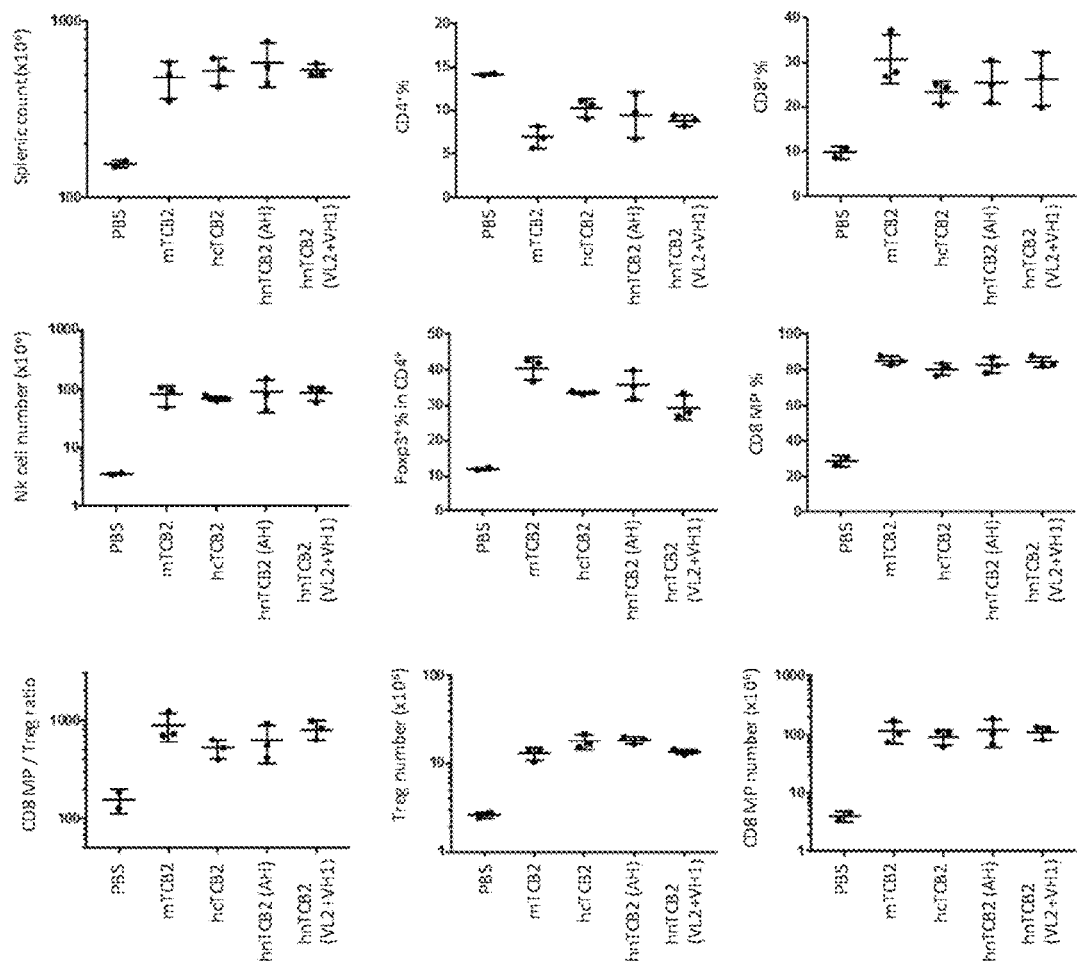
FIG. 9 shows the in vivo immunostimulatory of a hIL-2/hnTCB2 complex and the results of experimental statistical analysis.

To compare the immune cell activation function between original mouse TCB2, human chimeric TCB2 (hcTCB2) and humanized TCB2 (hnTCB2), hIL-2 was allowed to form complexes with different TCB2s (mouse TCB2 (mTCB2), hcTCB2, and hnTCB2). Each of the complexes was injected into B6 mice once a day from day 0 to day 3 (four times), and on day 5, the splenic immune cells were analyzed by flow cytometry. As a result, it was shown that the affinity of hnTCB2 was slightly lower than that of mTCB2 or hcTCB2 (Table 8), but the function of hnTCB2 to activate immune cells was similar to that of mTCB2 (FIG. 9; VL2+VH2 was not indicated due to its low functionality). Thus, it was demonstrated that mTCB2 was successfully humanized.

Figure 10:
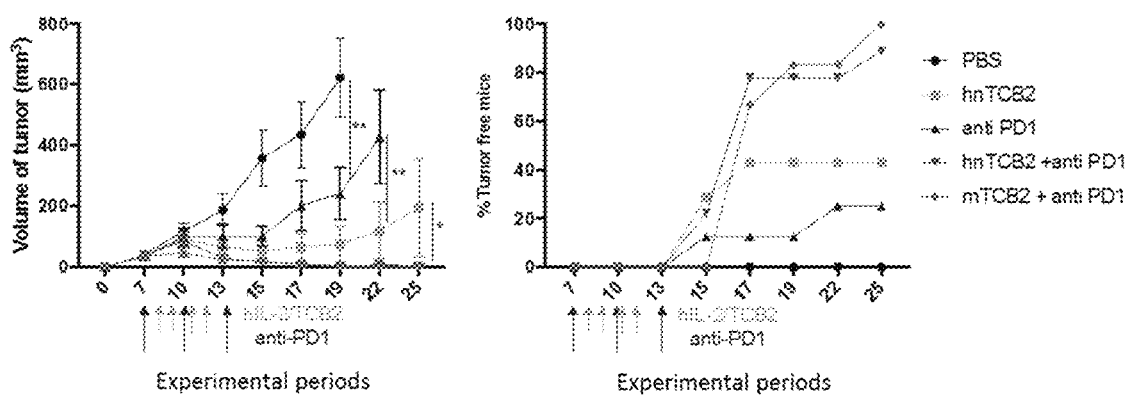
FIG. 10 shows the anti-tumor effect of a combination of a hIL-2/hnTCB2 complex and an anti-PD-1 antibody in MC38 tumor models (B6 colon cancer) (*$p<0.05$, **$p<0.01$ (Two way ANOVA for day 19 and 22, unpaired t test for day 25)).

In order to examine whether hnTCB2 has anticancer activity in addition to the function of activating immune cells, $5 \times 10^5$ MC38 cells were injected subcutaneously into B6 mice on day 0, and anti-PD-1 antibody (200 µg) was injected three times at 3-day intervals from day 7. Next, the hIL-2/hnTCB2 (VL2+VH1, 1.5 µg/15µ) complex was injected once a day from day 8 to day 11 (four times), and then growth of the MC38 tumor was observed. As a result, growth of the tumor was delayed even by treatment with a high concentration of the anti-PD-1 antibody alone, but when the mice were treated with the hIL-2/hnTCB2 complex, growth of the MC38 tumor was strongly inhibited to a level similar to a level shown in treatment with the hIL-2/mTCB2 complex, and the tumor was rejected in 40% of the mice. When the hIL-2/hnTCB2 or hIL-2/mTCB2 complex was injected together with the anti-PD-1 antibody, the tumor was rejected in 85% of the mice (FIG. 10). Thus, it was confirmed that the function of original mTCB2 was conserved in humanized TCB2.

INDUSTRIAL APPLICABILITY

The anti-hIL-2 antibody of the present invention binds specifically to a particular epitope of hIL-2, thereby inhibiting the binding of the hIL-2 to CD25, thereby minimizing expansion of Treg cells. In addition, it stimulates the $CD8^+$ T cells and NK cells that exhibit anti-tumor activity. Thus, the anti-hIL-2 antibody of the present invention is useful as a new anticancer therapeutic agent.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. An anti-hIL-2 antibody or antigen-binding fragment thereof, which binds specifically to human interleukin-2 (hIL-2), and inhibits the binding of the hIL-2 to CD25, wherein the anti-hIL-2 antibody or antigen-binding fragment thereof comprises:
   a heavy-chain variable region comprising a heavy-chain CDR1 comprising the amino acid sequence of SEQ ID NO: 11, a heavy-chain CDR2 comprising the amino acid sequence of SEQ ID NO: 12, and a heavy-chain CDR3 comprising the amino acid sequence of SEQ ID NO: 13; and
   a light-chain variable region comprising a light-chain CDR1 comprising the amino acid sequence of SEQ ID NO: 14, a light-chain CDR2 comprising the amino acid sequence of SEQ ID NO: 15, and a light-chain CDR3 comprising the amino acid sequence of SEQ ID NO: 16.

2. The anti-hIL-2 antibody of claim 1, wherein the antibody is a chimeric or humanized antibody.

3. The anti-hIL-2 antibody or antigen-binding fragment thereof of claim 1, wherein the anti-hIL-2 antibody or antigen-binding fragment thereof comprises:
   a heavy-chain variable region comprising the amino acid sequence selected from the group consisting of SEQ ID NOS: 3, 23, 28, 32, and 34; and
   a light-chain variable region comprising the amino acid sequence selected from the group consisting of SEQ ID NOS: 4, 24, 26, and 30.

4. The anti-hIL-2 antibody or antigen-binding fragment thereof of claim 3, wherein the anti-hIL-2 antibody or antigen-binding fragment thereof comprises:
   a heavy-chain variable region of SEQ ID NO: 3 and a light-chain variable region of SEQ ID NO: 4;
   a heavy-chain variable region of SEQ ID NO: 23 and a light-chain variable region of SEQ ID NO: 24;

a heavy-chain variable region of SEQ ID NO: 28 and a light-chain variable region of SEQ ID NO: 26;

a heavy-chain variable region of SEQ ID NO: 32 and a light-chain variable region of SEQ ID NO: 30; or a heavy-chain variable region of SEQ ID NO: 34 and a light-chain variable region of SEQ ID NO: 30.

5. The anti-hIL-2 antibody or antigen-binding fragment thereof of claim 1, wherein the anti-hIL-2 antibody or antigen-binding fragment thereof induces expansion of CD8+ T cells and NK cells.

6. A nucleic acid encoding the anti-hIL-2 antibody or antigen-binding fragment thereof of claim 1.

7. A recombinant vector comprising the nucleic acid of claim 6.

8. A cell transformed with the recombinant vector of claim 7.

9. A method of producing an anti-hIL-2 antibody or antigen-binding fragment thereof, comprising culturing the cell of claim 8.

10. A complex comprising the anti-hIL-2 antibody or antigen-binding fragment of claim 1 and hIL-2, wherein the anti-hIL-2 antibody or antigen-binding fragment is bound to hIL-2.

* * * * *